US009745602B2

(12) United States Patent
Daviet et al.

(10) Patent No.: US 9,745,602 B2
(45) Date of Patent: Aug. 29, 2017

(54) MODIFIED MICROORGANISMS AND USE THEREOF FOR TERPENE PRODUCTION

(75) Inventors: Laurent Daviet, Geneva (CH); Michel Schalk, Geneva (CH); Jens Nielsen, Gothenburg (SE); Verena Siewers, Göteborg (SE); Christoph Knuf, Göteborg (SE); Gionata Scalcinati, Cavenago Bza (IT)

(73) Assignee: FIRMENICH SA, Geneva (CH)

( * ) Notice: Subject to any disclaimer, the term of this patent is extended or adjusted under 35 U.S.C. 154(b) by 437 days.

(21) Appl. No.: 14/128,074

(22) PCT Filed: Jun. 1, 2012

(86) PCT No.: PCT/EP2012/060362

§ 371 (c)(1), (2), (4) Date: Dec. 20, 2013

(87) PCT Pub. No.: WO2013/000660

PCT Pub. Date: Jan. 3, 2013

(65) Prior Publication Data

US 2014/0113343 A1 Apr. 24, 2014

Related U.S. Application Data

(60) Provisional application No. 61/501,509, filed on Jun. 27, 2011.

(30) Foreign Application Priority Data

Jun. 28, 2011 (EP) .................................... 11171612
Nov. 2, 2011 (EP) .................................... 11187433

(51) Int. Cl.

| | |
|---|---|
| ***C12P 5/00*** | (2006.01) |
| ***C12N 15/00*** | (2006.01) |
| ***C12N 1/20*** | (2006.01) |
| ***C12N 9/10*** | (2006.01) |
| ***C12N 1/14*** | (2006.01) |
| ***C12Q 1/68*** | (2006.01) |
| ***C07H 21/04*** | (2006.01) |
| ***C12P 5/02*** | (2006.01) |
| ***C12N 9/88*** | (2006.01) |
| ***C12N 15/81*** | (2006.01) |
| ***C12N 15/63*** | (2006.01) |

(52) U.S. Cl.

CPC ............ *C12P 5/026* (2013.01); *C12N 9/1085* (2013.01); *C12N 9/88* (2013.01); *C12N 15/635* (2013.01); *C12N 15/81* (2013.01); *C12P 5/002* (2013.01); *C12P 5/007* (2013.01); *C12P 5/02* (2013.01)

(58) Field of Classification Search

None

See application file for complete search history.

(56) References Cited

FOREIGN PATENT DOCUMENTS

| | | | |
|---|---|---|---|
| WO | WO2008/151149 | A2 | 12/2008 |
| WO | WO2009/109597 | A8 | 9/2009 |
| WO | WO2010/019696 | A3 | 2/2010 |

OTHER PUBLICATIONS

Li et al. Usage of an intronic promoter for stable gene expression in *Saccharomyces cerevisiae*. Letters in Applied Microbiology 2005, 40, 347-352.*
Hiroaki Inoue et al. Gene, 96 (1990) 23-28.
Xicheng Mao et al. Current Microbiology vol. 45 (2002), pp. 37-40.
Dae-Kyun Ro et al. Nature vol. 440 Apr. 13, 2006.
International Search Report and Written Opinion, application PCT/EP2012/060362, mailed Sep. 19, 2012.
Mohammad A. Asasollahi et al. Biotechnology and Bioengineering vol. 99, No. 3, Feb. 15, 2008.
Mohammad A. Asadollahi et al. Biotechnology and Bioengineering vol. 106, No. 1, May 1, 2010.
José Manuel Otero et al. Otero et al. BMC Genomics 2010, 11:723.
Alexander Faulkner et al. J. Biol. Chem,1999, 274:14831-14837.
Jasper A. Diderich et al. J. Biol. Chem. 1999, 274:15350-15359.
Ulrich Güldener et al. Nucleic Acids Research, 1996, vol. 24, No. 13 2519-2524.
Siavash Partow et al. Yeast 2010 ; 27: 955-964.
Verduyn, C., et al., Yeast, vol. 8: 501-517 (1992).
Erdeniz, N., et al., Genome Research, 7:1174-1183 (1997).
Flagfeldt, D. B. et al., Yeast, 26: 545-551 (2009).
Jennings, S.M., et al., Squalene synthetase [*Saccharomyces cerevisiae*], GenBank Accession No. AAA34597, Aug. 13, 2008.
Rocci, L., et al., Clausena lansium Tps2-1 mRNA, complete cds, GenBank Accession No. HQ452480, Dec. 11, 2010.
Jacq, C., et al.,*Saccharomyces cerevisiae* S288c phosphatidate phosphatase LPP1 (LPP1), partial mRNA, GenBank Accession No. NM_001180811, Mar. 15, 2017.

* cited by examiner

*Primary Examiner* — Yong Pak

(57) ABSTRACT

The present invention relates to the control of gene expression by a heterologous glucose-regulated promoter, to microorganisms in which gene expression is controlled by a heterologous glucose-regulated promoter and to methods using said microorganisms for the production of terpenes during glucose-limited fed-batch fermentation.

13 Claims, 3 Drawing Sheets

SEQUENCE LISTING

```
<160> NUMBER OF SEQ ID NOS: 48

<210> SEQ ID NO 1
<211> LENGTH: 36
<212> TYPE: DNA
<213> ORGANISM: Artificial sequence
<220> FEATURE:
<223> OTHER INFORMATION: Primer

<400> SEQUENCE: 1

ggactagtcc ttggtataag gtgagggggt ccacag                                36


<210> SEQ ID NO 2
<211> LENGTH: 38
<212> TYPE: DNA
<213> ORGANISM: Artificial sequence
<220> FEATURE:
<223> OTHER INFORMATION: Primer

<400> SEQUENCE: 2

tccccgcggg gagaatacca ccgtgaggag caggcatg                              38


<210> SEQ ID NO 3
<211> LENGTH: 40
<212> TYPE: DNA
<213> ORGANISM: Artificial sequence
<220> FEATURE:
<223> OTHER INFORMATION: Primer

<400> SEQUENCE: 3

gatccccggg aattgccatg acgctgcagg tcgacaaccc                            40


<210> SEQ ID NO 4
<211> LENGTH: 23
<212> TYPE: DNA
<213> ORGANISM: Artificial sequence
<220> FEATURE:
<223> OTHER INFORMATION: Primer

<400> SEQUENCE: 4

ccatgagtga cgactgaatc cgg                                              23
```

<210> SEQ ID NO 5
<211> LENGTH: 23
<212> TYPE: DNA
<213> ORGANISM: Artificial sequence
<220> FEATURE:
<223> OTHER INFORMATION: Primer

<400> SEQUENCE: 5
ctatcgattg tatgggaagc ccg 23

<210> SEQ ID NO 6
<211> LENGTH: 59
<212> TYPE: DNA
<213> ORGANISM: Artificial sequence
<220> FEATURE:
<223> OTHER INFORMATION: Primer

<400> SEQUENCE: 6
caatgccaat tgtaatagct tcccatgtta attatacttt attcttgtta ttattatac 59

<210> SEQ ID NO 7
<211> LENGTH: 22
<212> TYPE: DNA
<213> ORGANISM: Artificial sequence
<220> FEATURE:
<223> OTHER INFORMATION: Primer

<400> SEQUENCE: 7
agcctcagta cgctggtacc cg 22

<210> SEQ ID NO 8
<211> LENGTH: 45
<212> TYPE: DNA
<213> ORGANISM: Artificial sequence
<220> FEATURE:
<223> OTHER INFORMATION: Primer

<400> SEQUENCE: 8
catggcaatt cccggggatc tgggctatga aatgtactga gtcag 45

<210> SEQ ID NO 9
<211> LENGTH: 27
<212> TYPE: DNA
<213> ORGANISM: Artificial sequence
<220> FEATURE:
<223> OTHER INFORMATION: Primer

<400> SEQUENCE: 9
atgggaaagc tattacaatt ggcattg 27

<210> SEQ ID NO 10
<211> LENGTH: 22
<212> TYPE: DNA
<213> ORGANISM: Artificial sequence
<220> FEATURE:
<223> OTHER INFORMATION: Primer

<400> SEQUENCE: 10
gtcgtagtcg tggacggttt gc 22

<210> SEQ ID NO 11
<211> LENGTH: 20
<212> TYPE: DNA
<213> ORGANISM: Artificial sequence
<220> FEATURE:

<223> OTHER INFORMATION: Primer

<400> SEQUENCE: 11
aaggatgatc tctgtcatgg 20

<210> SEQ ID NO 12
<211> LENGTH: 40
<212> TYPE: DNA
<213> ORGANISM: Artificial sequence
<220> FEATURE:
<223> OTHER INFORMATION: Primer

<400> SEQUENCE: 12
gatccccggg aattgccatg tgttagggca gcatttatgc 40

<210> SEQ ID NO 13
<211> LENGTH: 42
<212> TYPE: DNA
<213> ORGANISM: Artificial sequence
<220> FEATURE:
<223> OTHER INFORMATION: Primer

<400> SEQUENCE: 13
gcagggatgc ggccgctgac gcactccaag cggacattca ag 42

<210> SEQ ID NO 14
<211> LENGTH: 20
<212> TYPE: DNA
<213> ORGANISM: Artificial sequence
<220> FEATURE:
<223> OTHER INFORMATION: Primer

<400> SEQUENCE: 14
gaagtatgtc tcttttcgcc 20

<210> SEQ ID NO 15
<211> LENGTH: 49
<212> TYPE: DNA
<213> ORGANISM: Artificial sequence
<220> FEATURE:
<223> OTHER INFORMATION: Primer

<400> SEQUENCE: 15
catggcaatt cccggggatc cccttaatat aacttcgtat aatgtatgc 49

<210> SEQ ID NO 16
<211> LENGTH: 23
<212> TYPE: DNA
<213> ORGANISM: Artificial sequence
<220> FEATURE:
<223> OTHER INFORMATION: Primer

<400> SEQUENCE: 16
ccatgagtga cgactgaatc cgg 23

<210> SEQ ID NO 17
<211> LENGTH: 21
<212> TYPE: DNA
<213> ORGANISM: Artificial sequence
<220> FEATURE:
<223> OTHER INFORMATION: Primer

<400> SEQUENCE: 17
gcaaaggtag cgttgccaat g 21

```
<210> SEQ ID NO 18
<211> LENGTH: 41
<212> TYPE: DNA
<213> ORGANISM: Artificial sequence
<220> FEATURE:
<223> OTHER INFORMATION: Primer

<400> SEQUENCE: 18

gtcagcggcc gcatccctgc cgactcacta tagggagacc g                          41


<210> SEQ ID NO 19
<211> LENGTH: 25
<212> TYPE: DNA
<213> ORGANISM: Artificial sequence
<220> FEATURE:
<223> OTHER INFORMATION: Primer

<400> SEQUENCE: 19

tagttgccac gtgaaacctg acaac                                            25


<210> SEQ ID NO 20
<211> LENGTH: 25
<212> TYPE: DNA
<213> ORGANISM: Artificial sequence
<220> FEATURE:
<223> OTHER INFORMATION: Primer

<400> SEQUENCE: 20

aatttcatcg gtattttggc ttcgg                                            25


<210> SEQ ID NO 21
<211> LENGTH: 52
<212> TYPE: DNA
<213> ORGANISM: Artificial sequence
<220> FEATURE:
<223> OTHER INFORMATION: Primer

<400> SEQUENCE: 21

cgaagttatt aggtgatatc agatccactg cccatcttca acaacaatac cg              52


<210> SEQ ID NO 22
<211> LENGTH: 22
<212> TYPE: DNA
<213> ORGANISM: Artificial sequence
<220> FEATURE:
<223> OTHER INFORMATION: Primer

<400> SEQUENCE: 22

gtcgtagtcg tggacggttt gc                                               22


<210> SEQ ID NO 23
<211> LENGTH: 56
<212> TYPE: DNA
<213> ORGANISM: Artificial sequence
<220> FEATURE:
<223> OTHER INFORMATION: Primer

<400> SEQUENCE: 23

cgaagttatt aggtgatatc agatccactt gcaggtctca tctggaatat aattcc          56


<210> SEQ ID NO 24
<211> LENGTH: 83
<212> TYPE: DNA
<213> ORGANISM: Artificial sequence
<220> FEATURE:
<223> OTHER INFORMATION: Primer
```

<400> SEQUENCE: 24
gctgccttca tctcgaccgg atgcaatgcc aattgtaata gctttcccat gattttacgt 60
atatcaacta gttgacgatt atg 83

<210> SEQ ID NO 25
<211> LENGTH: 71
<212> TYPE: DNA
<213> ORGANISM: Artificial sequence
<220> FEATURE:
<223> OTHER INFORMATION: Primer

<400> SEQUENCE: 25
gagtgaacct gctgcctggc gtgctctgac tcagtacatt tcatagccca gtacgctgca 60
ggtcgacaac c 71

<210> SEQ ID NO 26
<211> LENGTH: 29
<212> TYPE: DNA
<213> ORGANISM: Artificial sequence
<220> FEATURE:
<223> OTHER INFORMATION: Primer

<400> SEQUENCE: 26
agtggatctg atatcaccta ataacttcg 29

<210> SEQ ID NO 27
<211> LENGTH: 33
<212> TYPE: DNA
<213> ORGANISM: Artificial sequence
<220> FEATURE:
<223> OTHER INFORMATION: Primer

<400> SEQUENCE: 27
ccttgcttac acagagtgaa cctgctgcct ggc 33

<210> SEQ ID NO 28
<211> LENGTH: 32
<212> TYPE: DNA
<213> ORGANISM: Artificial sequence
<220> FEATURE:
<223> OTHER INFORMATION: Primer

<400> SEQUENCE: 28
cttcagcttc aaagctgcct tcatctcgac cg 32

<210> SEQ ID NO 29
<211> LENGTH: 45
<212> TYPE: DNA
<213> ORGANISM: Artificial sequence
<220> FEATURE:
<223> OTHER INFORMATION: Primer

<400> SEQUENCE: 29
gttgttgcgg ccgcaaaaca atgtcaactc aacaagtttc atcag 45

<210> SEQ ID NO 30
<211> LENGTH: 35
<212> TYPE: DNA
<213> ORGANISM: Artificial sequence
<220> FEATURE:
<223> OTHER INFORMATION: Primer

<400> SEQUENCE: 30
gttgttttaa ttaactaatc gtcaagctta acggg 35

<210> SEQ ID NO 31
<211> LENGTH: 34
<212> TYPE: DNA
<213> ORGANISM: Artificial sequence
<220> FEATURE:
<223> OTHER INFORMATION: Primer

<400> SEQUENCE: 31
gttgttgcta gcttaggatt taatgcaggt gacg 34

<210> SEQ ID NO 32
<211> LENGTH: 20
<212> TYPE: DNA
<213> ORGANISM: Artificial sequence
<220> FEATURE:
<223> OTHER INFORMATION: Primer

<400> SEQUENCE: 32
ggttccgcgc acatttcccc 20

<210> SEQ ID NO 33
<211> LENGTH: 35
<212> TYPE: DNA
<213> ORGANISM: Artificial sequence
<220> FEATURE:
<223> OTHER INFORMATION: Primer

<400> SEQUENCE: 33
caacaaaagc ttgtataagg tgagggggtc cacag 35

<210> SEQ ID NO 34
<211> LENGTH: 52
<212> TYPE: DNA
<213> ORGANISM: Artificial sequence
<220> FEATURE:
<223> OTHER INFORMATION: Primer

<400> SEQUENCE: 34
caacaaggcg gccgcgttaa ttatacttta ttcttgttat tattatactt tc 52

<210> SEQ ID NO 35
<211> LENGTH: 1061
<212> TYPE: DNA
<213> ORGANISM: Saccharomyces cerevisiae

<400> SEQUENCE: 35
gatccccggg aattgccatg acgctgcagg tcgacaaccc ttaatataac ttcgtataat 60
gtatgctata cgaagttatt aggtctagag atctgtttag cttgcctcgt ccccgccggg 120
tcacccggcc agcgacatgg aggcccagaa taccctcctt gacagtcttg acgtgcgcag 180
ctcaggggca tgatgtgact gtcgcccgta catttagccc atacatcccc atgtataatc 240
atttgcatcc atacattttg atggccgcac ggcgcgaagc aaaaattacg gctcctcgct 300
gcagacctgc gagcagggaa acgctcccct cacagacgcg ttgaattgtc cccacgccgc 360
gcccctgtag agaaatataa aaggttagga tttgccactg aggttcttct ttcatatact 420
tccttttaaa atcttgctag gatacagttc tcacatcaca tccgaacata aacaaccatg 480
ggtaaggaaa agactcacgt ttcgaggccg cgattaaatt ccaacatgga tgctgattta 540
tatgggtata aatgggctcg cgataatgtc gggcaatcag gtgcgacaat ctatcgattg 600
tatgggaagc ccgatgcgcc agagttgttt ctgaaacatg gcaaaggtag cgttgccaat 660

```
gatgttacag atgagatggt cagactaaac tggctgacgg aatttatgcc tcttccgacc    720

atcaagcatt ttatccgtac tcctgatgat gcatggttac tcaccactgc gatccccggc    780

aaaacagcat tccaggtatt agaagaatat cctgattcag gtgaaaatat tgttgatgcg    840

ctggcagtgt tcctgcgccg gttgcattcg attcctgttt gtaattgtcc ttttaacagc    900

gatcgcgtat ttcgtctcgc tcaggcgcaa tcacgaatga ataacggttt ggttgatgcg    960

agtgattttg atgacgagcg taatggctgg cctgttgaac aagtctggaa agaaatgcat   1020

aagcttttgc cattctcacc ggattcagtc gtcactcatg g                       1061
```

```
<210> SEQ ID NO 36
<211> LENGTH: 1582
<212> TYPE: DNA
<213> ORGANISM: Saccharomyces cerevisiae

<400> SEQUENCE: 36

ctatcgattg tatgggaagc ccgatgcgcc agagttgttt ctgaaacatg gcaaaggtag     60

cgttgccaat gatgttacag atgagatggt cagactaaac tggctgacgg aatttatgcc    120

tcttccgacc atcaagcatt ttatccgtac tcctgatgat gcatggttac tcaccactgc    180

gatccccggc aaaacagcat tccaggtatt agaagaatat cctgattcag gtgaaaatat    240

tgttgatgcg ctggcagtgt tcctgcgccg gttgcattcg attcctgttt gtaattgtcc    300

ttttaacagc gatcgcgtat ttcgtctcgc tcaggcgcaa tcacgaatga ataacggttt    360

ggttgatgcg agtgattttg atgacgagcg taatggctgg cctgttgaac aagtctggaa    420

agaaatgcat aagcttttgc cattctcacc ggattcagtc gtcactcatg gtgatttctc    480

acttgataac cttatttttg acgaggggaa attaataggt tgtattgatg ttggacgagt    540

cggaatcgca gaccgatacc aggatcttgc catcctatgg aactgcctcg gtgagttttc    600

tccttcatta cagaaacggc tttttcaaaa atatggtatt gataatcctg atatgaataa    660

attgcagttt catttgatgc tcgatgagtt tttctaatca gtactgacaa taaaaagatt    720

cttgttttca agaacttgtc atttgtatag tttttttata ttgtagttgt tctattttaa    780

tcaaatgtta gcgtgattta tatttttttt cgcctcgaca tcatctgccc agatgcgaag    840

ttaagtgcgc agaaagtaat atcatgcgtc aatcgtatgt gaatgctggt cgctatactg    900

ctgtcgattc gatactaacg ccgccatcca gtgtcgaaaa cgagctctcg agaaccctta    960

atataacttc gtataatgta tgctatacga agttattagg tgatatcaga tccactagtc   1020

cttggtataa ggtgaggggg tccacagata taacatcgtt taatttagta ctaacagaga   1080

cttttgtcac aactacatat aagtgtacaa atatagtaca gatatgacac acttgtagcg   1140

ccaacgcgca tcctacggat tgctgacaga aaaaaaggtc acgtgaccag aaaagtcacg   1200

tgtaattttg taactcaccg cattctagcg gtccctgtcg tgcacactgc actcaacacc   1260

ataaacctta gcaacctcca aaggaaatca ccgtataaca aagccacagt tttacaactt   1320

agtctcttat gaagttactt accaatgaga aatagaggct ctttctcgag aaatatgaat   1380

atggatatat atatatatat atatatatat atatatatat atgtaaactt ggttcttttt   1440

tagcttgtga tctctagctt gggtctctct ctgtcgtaac agttgtgata tcgtttctta   1500

acaattgaaa aggaactaag aaagtataat aataacaaga ataaagtata attaacatgg   1560

gaagctatta caattggcat tg                                            1582
```

```
<210> SEQ ID NO 37
<211> LENGTH: 551
```

<212> TYPE: DNA
<213> ORGANISM: Saccharomyces cerevisiae

<400> SEQUENCE: 37

```
agcctcagta cgctggcacc cgtcacaatg tagggctata tatgctggag ctgctacgaa     60

agcggcttgg tctgcagggg agaacttatt cccctgtgcc taatacgggc ggcaaagtgc    120

attatataga agacgaacat tgtacgatac taagatcgga tggccagtac atgaatctaa    180

gtggagaaca ggtgtgcaag gtctgggccc ggtacgccaa gtaccaagcc cgacacgttg    240

ttattcatga cgagttaagt gtggcgtgtg gaaaagtgca gctcagagcc cccagcacca    300

gtattagagg tcataatggg ctgcgaagcc tgctaaaatg cagtggaggc cgtgtaccct    360

ttgccaaatt ggctattgga atcggcagag aacctgggtc ccgttctaga gaccctgcga    420

gcgtgtcccg gtgggttctg ggagctctaa ctccgcagga actacaaacc ttgcttacac    480

agagtgaacc tgctgcctgg cgtgctctga ctcagtacat ttcatagccc agatccccgg    540

gaattgccat g                                                         551
```

<210> SEQ ID NO 38
<211> LENGTH: 528
<212> TYPE: DNA
<213> ORGANISM: Saccharomyces cerevisiae

<400> SEQUENCE: 38

```
atgggaaagc tattacaatt ggcattgcat ccggtcgaga tgaaggcagc tttgaagctg     60

aagttttgca gaacaccgct attctccatc tatgatcagt ccacgtctcc atatctcttg    120

cactgtttcg aactgttgaa cttgacctcc agatcgtttg ctgctgtgat cagagagctg    180

catccagaat tgagaaactg tgttactctc ttttatttga ttttaagggc tttggatacc    240

atcgaagacg atatgtccat cgaacacgat ttgaaaattg acttgttgcg tcacttccac    300

gagaaattgt tgttaactaa atggagtttc gacggaaatg cccccgatgt gaaggacaga    360

gccgttttga cagatttcga atcgattctt attgaattcc acaaattgaa accagaatat    420

caagaagtca tcaaggagat caccgagaaa atgggtaatg gtatggccga ctacatcttg    480

gatgaaaatt acaacttgaa tgggttgcaa accgtccacg actacgac                 528
```

<210> SEQ ID NO 39
<211> LENGTH: 1592
<212> TYPE: DNA
<213> ORGANISM: Saccharomyces cerevisiae

<400> SEQUENCE: 39

```
agcctcagta cgctggcacc cgtcacaatg tagggctata tatgctggag ctgctacgaa     60

agcggcttgg tctgcagggg agaacttatt cccctgtgcc taatacgggc ggcaaagtgc    120

attatataga agacgaacat tgtacgatac taagatcgga tggccagtac atgaatctaa    180

gtggagaaca ggtgtgcaag gtctgggccc ggtacgccaa gtaccaagcc cgacacgttg    240

ttattcatga cgagttaagt gtggcgtgtg gaaaagtgca gctcagagcc cccagcacca    300

gtattagagg tcataatggg ctgcgaagcc tgctaaaatg cagtggaggc cgtgtaccct    360

ttgccaaatt ggctattgga atcggcagag aacctgggtc ccgttctaga gaccctgcga    420

gcgtgtcccg gtgggttctg ggagctctaa ctccgcagga actacaaacc ttgcttacac    480

agagtgaacc tgctgcctgg cgtgctctga ctcagtacat ttcatagccc agatccccgg    540

gaattgccat gacgctgcag gtcgacaacc cttaatataa cttcgtataa tgtatgctat    600
```

-continued

```
acgaagttat taggtctaga gatctgttta gcttgcctcg tccccgccgg gtcacccggc    660

cagcgacatg gaggcccaga ataccctcct tgacagtctt gacgtgcgca gctcaggggc    720

atgatgtgac tgtcgcccgt acatttagcc catacatccc catgtataat catttgcatc    780

catacatttt gatggccgca cggcgcgaag caaaaattac ggctcctcgc tgcagacctg    840

cgagcaggga aacgctcccc tcacagacgc gttgaattgt ccccacgccg cgcccctgta    900

gagaaatata aaaggttagg atttgccact gaggttcttc tttcatatac ttccttttaa    960

aatcttgcta ggatacagtt ctcacatcac atccgaacat aaacaaccat gggtaaggaa   1020

aagactcacg tttcgaggcc gcgattaaat tccaacatgg atgctgattt atatgggtat   1080

aaatgggctc gcgataatgt cgggcaatca ggtgcgacaa tctatcgatt gtatgggaag   1140

cccgatgcgc cagagttgtt tctgaaacat ggcaaaggta gcgttgccaa tgatgttaca   1200

gatgagatgg tcagactaaa ctggctgacg gaatttatgc ctcttccgac catcaagcat   1260

tttatccgta ctcctgatga tgcatggtta ctcaccactg cgatccccgg caaaacagca   1320

ttccaggtat tagaagaata tcctgattca ggtgaaaata ttgttgatgc gctggcagtg   1380

ttcctgcgcc ggttgcattc gattcctgtt tgtaattgtc cttttaacag cgatcgcgta   1440

tttcgtctcg ctcaggcgca atcacgaatg aataacggtt tggttgatgc gagtgatttt   1500

gatgacgagc gtaatggctg gcctgttgaa caagtctgga aagaaatgca taagcttttg   1560

ccattctcac cggattcagt cgtcactcat gg                                 1592


<210> SEQ ID NO 40
<211> LENGTH: 2083
<212> TYPE: DNA
<213> ORGANISM: Saccharomyces cerevisiae

<400> SEQUENCE: 40

ctatcgattg tatgggaagc ccgatgcgcc agagttgttt ctgaaacatg gcaaaggtag     60

cgttgccaat gatgttacag atgagatggt cagactaaac tggctgacgg aatttatgcc    120

tcttccgacc atcaagcatt ttatccgtac tcctgatgat gcatggttac tcaccactgc    180

gatccccggc aaaacagcat tccaggtatt agaagaatat cctgattcag gtgaaaatat    240

tgttgatgcg ctggcagtgt tcctgcgccg gttgcattcg attcctgttt gtaattgtcc    300

ttttaacagc gatcgcgtat ttcgtctcgc tcaggcgcaa tcacgaatga ataacggttt    360

ggttgatgcg agtgattttg atgacgagcg taatggctgg cctgttgaac aagtctggaa    420

agaaatgcat aagcttttgc cattctcacc ggattcagtc gtcactcatg gtgatttctc    480

acttgataac cttatttttg acgaggggaa attaataggt tgtattgatg ttggacgagt    540

cggaatcgca gaccgatacc aggatcttgc catcctatgg aactgcctcg gtgagttttc    600

tccttcatta cagaaacggc tttttcaaaa atatggtatt gataatcctg atatgaataa    660

attgcagttt catttgatgc tcgatgagtt tttctaatca gtactgacaa taaaaagatt    720

cttgttttca agaacttgtc atttgtatag tttttttata ttgtagttgt tctattttaa    780

tcaaatgtta gcgtgattta tatttttttt cgcctcgaca tcatctgccc agatgcgaag    840

ttaagtgcgc agaaagtaat atcatgcgtc aatcgtatgt gaatgctggt cgctatactg    900

ctgtcgattc gatactaacg ccgccatcca gtgtcgaaaa cgagctctcg agaaccctta    960

atataacttc gtataatgta tgctatacga agttattagg tgatatcaga tccactagtc   1020

cttggtataa ggtgaggggg tccacagata taacatcgtt taatttagta ctaacagaga   1080

cttttgtcac aactacatat aagtgtacaa atatagtaca gatatgacac acttgtagcg   1140
```

```
ccaacgcgca tcctacggat tgctgacaga aaaaaaggtc acgtgaccag aaaagtcacg   1200

tgtaattttg taactcaccg cattctagcg gtccctgtcg tgcacactgc actcaacacc   1260

ataaacctta gcaacctcca aaggaaatca ccgtataaca aagccacagt tttacaactt   1320

agtctcttat gaagttactt accaatgaga aatagaggct ctttctcgag aaatatgaat   1380

atggatatat atatatatat atatatatat atatatatat atgtaaactt ggttcttttt   1440

tagcttgtga tctctagctt gggtctctct ctgtcgtaac agttgtgata tcgtttctta   1500

acaattgaaa aggaactaag aaagtataat aataacaaga ataaagtata attaacatgg   1560

gaagctatta caattggcat tgcatccggt cgagatgaag gcagctttga agctgaagtt   1620

ttgcagaaca ccgctattct ccatctatga tcagtccacg tctccatatc tcttgcactg   1680

tttcgaactg ttgaacttga cctccagatc gtttgctgct gtgatcagag agctgcatcc   1740

agaattgaga aactgtgtta ctctctttta tttgatttta agggctttgg ataccatcga   1800

agacgatatg tccatcgaac acgatttgaa aattgacttg ttgcgtcact tccacgagaa   1860

attgttgtta actaaatgga gtttcgacgg aaatgccccc gatgtgaagg acagagccgt   1920

tttgacagat ttcgaatcga ttcttattga attccacaaa ttgaaaccag aatatcaaga   1980

agtcatcaag gagatcaccg agaaaatggg taatggtatg gccgactaca tcttggatga   2040

aaattacaac ttgaatgggt tgcaaaccgt ccacgactac gac                     2083
```

```
<210> SEQ ID NO 41
<211> LENGTH: 420
<212> TYPE: DNA
<213> ORGANISM: Saccharomyces cerevisiae

<400> SEQUENCE: 41

aaggatgatc tctgtcatgg cggatgagaa acataaggag tattttaagc tatactactt     60

tcagtacatg ataattggtc tatgtacgat attattcctc tattcggaga tatccctggt    120

acctaggggc caaaacatcg aatttagtct tgatgacccc agtatatcaa aacgttatgt    180

acctaacgaa ctcgtgggcc cactagaatg tttgattttg agtgttggac tgagtaacat    240

ggtcgtcttc tggacctgca tgtttgacaa ggacttactg aagaagaata gagtaaagag    300

actaagagag aggccggacg gaatctcgaa cgattttcac ttcatgcata ctagcattct    360

atgtctgatg ctgattataa gcataaatgc tgccctaaca catggcaatt cccggggatc    420
```

```
<210> SEQ ID NO 42
<211> LENGTH: 275
<212> TYPE: DNA
<213> ORGANISM: Saccharomyces cerevisiae

<400> SEQUENCE: 42

gcagggatgc ggccgctgac gcactccaag cggacattca agtttcatag tcagtaccat     60

gggctttaca tatctttggc aaagggtttt caccacacgc aatacaagaa gttgcatttg    120

gtgcccttta ttagctctag tagtaatggt ttcaagggtt atcgatcaca gacatcattg    180

gtacgatgtt gtctctggag ctgttctagc atttttagtc atttattgtt gctggaaatg    240

gacatttaca aacttggcga aaagagacat acttc                              275
```

```
<210> SEQ ID NO 43
<211> LENGTH: 1044
<212> TYPE: DNA
<213> ORGANISM: Saccharomyces cerevisiae
```

<400> SEQUENCE: 43

```
catggcaatt cccggggatc cccttaatat aacttcgtat aatgtatgct atacgaagtt      60
attaggtcta gagatctgtt tagcttgcct cgtccccgcc gggtcacccg gccagcgaca     120
tggaggccca gaataccctc cttgacagtc ttgacgtgcg cagctcaggg gcatgatgtg     180
actgtcgccc gtacatttag cccatacatc cccatgtata atcatttgca tccatacatt     240
ttgatggccg cacggcgcga agcaaaaatt acggctcctc gctgcagacc tgcgagcagg     300
gaaacgctcc cctcacagac gcgttgaatt gtccccacgc cgcgcccctg tagagaaata     360
taaaaggtta ggatttgcca ctgaggttct tctttcatat acttcctttt aaaatcttgc     420
taggatacag ttctcacatc acatccgaac ataaacaacc atgggtaagg aaaagactca     480
cgtttcgagg ccgcgattaa attccaacat ggatgctgat ttatatgggt ataaatgggc     540
tcgcgataat gtcgggcaat caggtgcgac aatctatcga ttgtatggga agcccgatgc     600
gccagagttg tttctgaaac atggcaaagg tagcgttgcc aatgatgtta cagatgagat     660
ggtcagacta aactggctga cggaatttat gcctcttccg accatcaagc attttatccg     720
tactcctgat gatgcatggt tactcaccac tgcgatcccc ggcaaaacag cattccaggt     780
attagaagaa tatcctgatt caggtgaaaa tattgttgat gcgctggcag tgttcctgcg     840
ccggttgcat tcgattcctg tttgtaattg tccttttaac agcgatcgcg tatttcgtct     900
cgctcaggcg caatcacgaa tgaataacgg tttggttgat gcgagtgatt ttgatgacga     960
gcgtaatggc tggcctgttg aacaagtctg gaaagaaatg cataagcttt tgccattctc    1020
accggattca gtcgtcactc atgg                                           1044
```

<210> SEQ ID NO 44
<211> LENGTH: 1033
<212> TYPE: DNA
<213> ORGANISM: Saccharomyces cerevisiae

<400> SEQUENCE: 44

```
gcaaaggtag cgttgccaat gatgttacag atgagatggt cagactaaac tggctgacgg      60
aatttatgcc tcttccgacc atcaagcatt ttatccgtac tcctgatgat gcatggttac     120
tcaccactgc gatccccggc aaaacagcat tccaggtatt agaagaatat cctgattcag     180
gtgaaaatat tgttgatgcg ctggcagtgt tcctgcgccg gttgcattcg attcctgttt     240
gtaattgtcc ttttaacagc gatcgcgtat ttcgtctcgc tcaggcgcaa tcacgaatga     300
ataacggttt ggttgatgcg agtgattttg atgacgagcg taatggctgg cctgttgaac     360
aagtctggaa agaaatgcat aagcttttgc cattctcacc ggattcagtc gtcactcatg     420
gtgatttctc acttgataac cttatttttg acgaggggaa attaataggt tgtattgatg     480
ttggacgagt cggaatcgca gaccgatacc aggatcttgc catcctatgg aactgcctcg     540
gtgagttttc tccttcatta cagaaacggc tttttcaaaa atatggtatt gataatcctg     600
atatgaataa attgcagttt catttgatgc tcgatgagtt tttctaatca gtactgacaa     660
taaaaagatt cttgttttca agaacttgtc atttgtatag tttttttata ttgtagttgt     720
tctattttaa tcaaatgtta gcgtgattta tatttttttt cgcctcgaca tcatctgccc     780
agatgcgaag ttaagtgcgc agaaagtaat atcatgcgtc aatcgtatgt gaatgctggt     840
cgctatactg ctgtcgattc gatactaacg ccgccatcca gtgtcgaaaa cgagctctcg     900
agaaccctta atataacttc gtataatgta tgctatacga agttattagg tgatatcaga     960
tccactagtg gcctatgcgg ccgcggatct gccggtctcc ctatagtgag tcggcaggga    1020
```

```
tgcggccgct gac                                                    1033

<210> SEQ ID NO 45
<211> LENGTH: 1444
<212> TYPE: DNA
<213> ORGANISM: Saccharomyces cerevisiae

<400> SEQUENCE: 45

aaggatgatc tctgtcatgg cggatgagaa acataaggag tattttaagc tatactactt    60

tcagtacatg ataattggtc tatgtacgat attattcctc tattcggaga tatccctggt   120

acctaggggc caaaacatcg aatttagtct tgatgacccc agtatatcaa aacgttatgt   180

acctaacgaa ctcgtgggcc cactagaatg tttgattttg agtgttggac tgagtaacat   240

ggtcgtcttc tggacctgca tgtttgacaa ggacttactg aagaagaata gagtaaagag   300

actaagagag aggccggacg gaatctcgaa cgattttcac ttcatgcata ctagcattct   360

atgtctgatg ctgattataa gcataaatgc tgccctaaca catggcaatt cccggggatc   420

cccttaatat aacttcgtat aatgtatgct atacgaagtt attaggtcta gagatctgtt   480

tagcttgcct cgtccccgcc gggtcacccg gccagcgaca tggaggccca gaataccctc   540

cttgacagtc ttgacgtgcg cagctcaggg gcatgatgtg actgtcgccc gtacatttag   600

cccatacatc cccatgtata atcatttgca tccatacatt ttgatggccg cacggcgcga   660

agcaaaaatt acggctcctc gctgcagacc tgcgagcagg gaaacgctcc cctcacagac   720

gcgttgaatt gtccccacgc cgcgcccctg tagagaaata taaaaggtta ggatttgcca   780

ctgaggttct tctttcatat acttcctttt aaaatcttgc taggatacag ttctcacatc   840

acatccgaac ataaacaacc atgggtaagg aaaagactca cgtttcgagg ccgcgattaa   900

attccaacat ggatgctgat ttatatgggt ataaatgggc tcgcgataat gtcgggcaat   960

caggtgcgac aatctatcga ttgtatggga agcccgatgc gccagagttg tttctgaaac  1020

atggcaaagg tagcgttgcc aatgatgtta cagatgagat ggtcagacta aactggctga  1080

cggaatttat gcctcttccg accatcaagc attttatccg tactcctgat gatgcatggt  1140

tactcaccac tgcgatcccc ggcaaaacag cattccaggt attagaagaa tatcctgatt  1200

caggtgaaaa tattgttgat gcgctggcag tgttcctgcg ccggttgcat tcgattcctg  1260

tttgtaattg tccttttaac agcgatcgcg tatttcgtct cgctcaggcg caatcacgaa  1320

tgaataacgg tttggttgat gcgagtgatt ttgatgacga gcgtaatggc tggcctgttg  1380

aacaagtctg gaaagaaatg cataagcttt tgccattctc accggattca gtcgtcactc  1440

atgg                                                              1444

<210> SEQ ID NO 46
<211> LENGTH: 1288
<212> TYPE: DNA
<213> ORGANISM: Saccharomyces cerevisiae

<400> SEQUENCE: 46

gcaaaggtag cgttgccaat gatgttacag atgagatggt cagactaaac tggctgacgg    60

aatttatgcc tcttccgacc atcaagcatt ttatccgtac tcctgatgat gcatggttac   120

tcaccactgc gatccccggc aaaacagcat tccaggtatt agaagaatat cctgattcag   180

gtgaaaatat tgttgatgcg ctggcagtgt tcctgcgccg gttgcattcg attcctgttt   240

gtaattgtcc ttttaacagc gatcgcgtat ttcgtctcgc tcaggcgcaa tcacgaatga   300
```

```
ataacggttt ggttgatgcg agtgattttg atgacgagcg taatggctgg cctgttgaac    360
aagtctggaa agaaatgcat aagcttttgc cattctcacc ggattcagtc gtcactcatg    420
gtgatttctc acttgataac cttatttttg acgaggggaa attaataggt tgtattgatg    480
ttggacgagt cggaatcgca gaccgatacc aggatcttgc catcctatgg aactgcctcg    540
gtgagttttc tccttcatta cagaaacggc tttttcaaaa atatggtatt gataatcctg    600
atatgaataa attgcagttt catttgatgc tcgatgagtt tttctaatca gtactgacaa    660
taaaaagatt cttgttttca agaacttgtc atttgtatag tttttttata ttgtagttgt    720
tctattttaa tcaaatgtta gcgtgattta tatttttttt cgcctcgaca tcatctgccc    780
agatgcgaag ttaagtgcgc agaaagtaat atcatgcgtc aatcgtatgt gaatgctggt    840
cgctatactg ctgtcgattc gatactaacg ccgccatcca gtgtcgaaaa cgagctctcg    900
agaaccctta atataacttc gtataatgta tgctatacga agttattagg tgatatcaga    960
tccactagtg gcctatgcgg ccgcggatct gccggtctcc ctatagtgag tcggcaggga   1020
tgcggccgct gacgcactcc aagcggacat tcaagtttca tagtcagtac catgggcttt   1080
acatatcttt ggcaaagggt tttcaccaca cgcaatacaa gaagttgcat ttggtgccct   1140
ttattagctc tagtagtaat ggtttcaagg gttatcgatc acagacatca ttggtacgat   1200
gttgtctctg gagctgttct agcattttta gtcatttatt gttgctggaa atggacattt   1260
acaaacttgg cgaaaagaga catacttc                                       1288
```

<210> SEQ ID NO 47
<211> LENGTH: 1959
<212> TYPE: DNA
<213> ORGANISM: Saccharomyces cerevisiae

<400> SEQUENCE: 47

```
ccttgcttac acagagtgaa cctgctgcct ggcgtgctct gactcagtac atttcatagc     60
ccagtacgct gcaggtcgac aacccttaat ataacttcgt ataatgtatg ctatacgaag    120
ttattaggtc tagagatctg tttagcttgc ctcgtccccg ccgggtcacc cggccagcga    180
catggaggcc cagaataccc tccttgacag tcttgacgtg cgcagctcag gggcatgatg    240
tgactgtcgc ccgtacattt agcccataca tccccatgta taatcatttg catccataca    300
ttttgatggc cgcacggcgc gaagcaaaaa ttacggctcc tcgctgcaga cctgcgagca    360
gggaaacgct cccctcacag acgcgttgaa ttgtccccac gccgcgcccc tgtagagaaa    420
tataaaaggt taggatttgc cactgaggtt cttctttcat atacttcctt ttaaaatctt    480
gctaggatac agttctcaca tcacatccga acataaacaa ccatgggtaa ggaaaagact    540
cacgtttcga ggccgcgatt aaattccaac atggatgctg atttatatgg gtataaatgg    600
gctcgcgata atgtcgggca atcaggtgcg acaatctatc gattgtatgg gaagcccgat    660
gcgccagagt tgtttctgaa acatggcaaa ggtagcgttg ccaatgatgt tacagatgag    720
atggtcagac taaactggct gacggaattt atgcctcttc cgaccatcaa gcattttatc    780
cgtactcctg atgatgcatg gttactcacc actgcgatcc ccggcaaaac agcattccag    840
gtattagaag aatatcctga ttcaggtgaa aatattgttg atgcgctggc agtgttcctg    900
cgccggttgc attcgattcc tgtttgtaat tgtcctttta acagcgatcg cgtatttcgt    960
ctcgctcagg cgcaatcacg aatgaataac ggtttggttg atgcgagtga ttttgatgac   1020
gagcgtaatg gctggcctgt tgaacaagtc tggaaagaaa tgcataagct tttgccattc   1080
tcaccggatt cagtcgtcac tcatggtgat ttctcacttg ataaccttat tttgacgag    1140
```

```
gggaaattaa taggttgtat tgatgttgga cgagtcggaa tcgcagaccg ataccaggat   1200
cttgccatcc tatggaactg cctcggtgag ttttctcctt cattacagaa acggcttttt   1260
caaaaatatg gtattgataa tcctgatatg aataaattgc agtttcattt gatgctcgat   1320
gagtttttct aatcagtact gacaataaaa agattcttgt tttcaagaac ttgtcatttg   1380
tatagttttt ttatattgta gttgttctat tttaatcaaa tgttagcgtg atttatattt   1440
tttttcgcct cgacatcatc tgcccagatg cgaagttaag tgcgcagaaa gtaatatcat   1500
gcgtcaatcg tatgtgaatg ctggtcgcta tactgctgtc gattcgatac taacgccgcc   1560
atccagtgtc gaaaacgagc tctcgagaac ccttaatata acttcgtata atgtatgcta   1620
tacgaagtta ttaggtgata tcagatccac tgcccatctt caacaacaat accgacttac   1680
catcctattt gctttgccct ttttcttttc cactgcactt tgcatcggaa ggcgttatcg   1740
gttttgggtt tagtgcctaa acgagcagcg agaacacgac cacgggctat ataaatggaa   1800
agttaggaca ggggcaaaga ataagagcac agaagaagag aaaagacgaa gagcagaagc   1860
ggaaaacgta tacacgtcac atatcacaca cacacaatgg gaaagctatt acaattggca   1920
ttgcatccgg tcgagatgaa ggcagctttg aagctgaag                           1959
```

<210> SEQ ID NO 48
<211> LENGTH: 2835
<212> TYPE: DNA
<213> ORGANISM: Saccharomyces cerevisiae

<400> SEQUENCE: 48

```
ccttgcttac acagagtgaa cctgctgcct ggcgtgctct gactcagtac atttcatagc     60
ccagtacgct gcaggtcgac aacccttaat ataacttcgt ataatgtatg ctatacgaag    120
ttattaggtc tagagatctg tttagcttgc ctcgtccccg ccgggtcacc cggccagcga    180
catggaggcc cagaataccc tccttgacag tcttgacgtg cgcagctcag gggcatgatg    240
tgactgtcgc ccgtacattt agcccataca tccccatgta taatcatttg catccataca    300
ttttgatggc cgcacggcgc gaagcaaaaa ttacggctcc tcgctgcaga cctgcgagca    360
gggaaacgct cccctcacag acgcgttgaa ttgtccccac gccgcgcccc tgtagagaaa    420
tataaaaggt taggatttgc cactgaggtt cttctttcat atacttcctt ttaaaatctt    480
gctaggatac agttctcaca tcacatccga acataaacaa ccatgggtaa ggaaaagact    540
cacgtttcga ggccgcgatt aaattccaac atggatgctg atttatatgg gtataaatgg    600
gctcgcgata atgtcgggca atcaggtgcg acaatctatc gattgtatgg gaagcccgat    660
gcgccagagt tgtttctgaa acatggcaaa ggtagcgttg ccaatgatgt tacagatgag    720
atggtcagac taaactggct gacggaattt atgcctcttc cgaccatcaa gcattttatc    780
cgtactcctg atgatgcatg gttactcacc actgcgatcc ccggcaaaac agcattccag    840
gtattagaag aatatcctga ttcaggtgaa aatattgttg atgcgctggc agtgttcctg    900
cgccggttgc attcgattcc tgtttgtaat tgtcctttta acagcgatcg cgtatttcgt    960
ctcgctcagg cgcaatcacg aatgaataac ggtttggttg atgcgagtga ttttgatgac   1020
gagcgtaatg gctggcctgt tgaacaagtc tggaaagaaa tgcataagct tttgccattc   1080
tcaccggatt cagtcgtcac tcatggtgat ttctcacttg ataaccttat ttttgacgag   1140
gggaaattaa taggttgtat tgatgttgga cgagtcggaa tcgcagaccg ataccaggat   1200
cttgccatcc tatggaactg cctcggtgag ttttctcctt cattacagaa acggcttttt   1260
```

-continued

```
caaaaatatg gtattgataa tcctgatatg aataaattgc agtttcattt gatgctcgat   1320

gagtttttct aatcagtact gacaataaaa agattcttgt tttcaagaac ttgtcatttg   1380

tatagttttt ttatattgta gttgttctat tttaatcaaa tgttagcgtg atttatattt   1440

tttttcgcct cgacatcatc tgcccagatg cgaagttaag tgcgcagaaa gtaatatcat   1500

gcgtcaatcg tatgtgaatg ctggtcgcta tactgctgtc gattcgatac taacgccgcc   1560

atccagtgtc gaaaacgagc tctcgagaac ccttaatata acttcgtata atgtatgcta   1620

tacgaagtta ttaggtgata tcagatccac ttgcaggtct catctggaat ataattcccc   1680

cctcctgaag caaaatttc ctttgagccg gaatttttga tattccgagt tcttttttc   1740

cattcgcgga ggttattcca ttcctaaacg agtggccaca atgaaacttc aattcatatc   1800

gaccgactat ttttctccga accaaaaaaa tagcagggcg agattggtgc tgcggaaaaa   1860

agaggaaaaa tttttttcgt agttttcttg tgcaaattag ggtgtaaggt ttttagggct   1920

tattggcaag cagaagagac gacaattata ggtcttaaat tcaaggcgga tgtaaggagt   1980

attggtttcg aaagtttttc cgaagcggca tggcagggac tgcttcgcat gcgctcggat   2040

tatcttcatt tttgcttgca aaaacgtaga atcatggtaa attacatgaa gaattctctt   2100

ttttttttt ttttttttt ttttacctct aaagagtgtt gaccaactga aaaaaccctt   2160

cttcaagaga gttaaactaa gactaaccat cataacttcc aaggaattaa tcgatatctt   2220

gcactcctga tttttcttca aagagacagc gcaaaggatt atgacactgt tgcattgagt   2280

caaaagtttt tccgaagtga cccagtgctc ttttttttt ttccgtgaag gactgacaaa   2340

tatgcgcaca agatccaata cgtaatggaa attcggaaaa actaggaaga aatgctgcag   2400

ggcattgccg tgccgatctt ttgtctttca gatatatgag aaaaagaata ttcatcaagt   2460

gctgatagaa gaataccact catatgacgt gggcagaaga cagcaaacgt aaacatgagc   2520

tgctgcgaca tttgatggct tttatccgac aagccaggaa actccaccat tatctaatgt   2580

agcaaaatat ttcttaacac ccgaagttgc gtgtcccccct cacgttttta atcatttgaa   2640

ttagtatatt gaaattatat ataaaggcaa caatgtcccc ataatcaatt ccatctgggg   2700

tctcatgttc tttccccacc ttaaaatcta taaagatatc ataatcgtca actagttgat   2760

atacgtaaaa tcatgggaaa gctattacaa ttggcattgc atccggtcga gatgaaggca   2820

gctttgaagc tgaag                                                    2835
```

MODIFIED MICROORGANISMS AND USE THEREOF FOR TERPENE PRODUCTION

TECHNICAL FIELD

The present invention relates to the control of gene expression by a heterologous glucose-regulated promoter, to microorganisms in which gene expression is controlled by a heterologous glucose-regulated promoter and to methods using said microorganisms for the production of terpenes during glucose-limited fed-batch fermentation.

PRIOR ART

Terpenes are found in most organisms (microorganisms, animals and plants). These compounds are made up of five carbon units called isoprene units and are classified by the number of these units present in their structure. Thus monoterpenes, sesquiterpenes and diterpenes are terpenes containing 10, 15 and 20 carbon atoms respectively. Sesquiterpenes, for example, are widely found in the plant kingdom. Many monoterpene, sesquiterpene and diterpene molecules are known for their flavor and fragrance properties and their cosmetic, medicinal and antimicrobial effects. Over 300 sesquiterpene hydrocarbons and 3,000 sesquiterpenoids have been identified and many new structures are identified each year. Plant extracts obtained by different means such as steam distillation or solvent extraction are used as source of terpenes. Terpene molecules are often used as such, but in some cases chemical reactions are used to transform the terpenes into other high value molecules.

Biosynthetic production of terpenes involves enzymes called terpene synthases. There is virtually an infinity of terpene synthases present in the plant kingdom, all using acyclic terpene precursors (mainly geranyl pyrophosphate (GPP), farnesyl pyrophosphate (FPP) or geranyl geranyl pyrophosphate (GGPP)) but having different product profiles. Genes and cDNAs encoding terpene synthases have been cloned and the corresponding recombinant enzymes characterized. The biosynthesis of terpenes in microorganisms has been extensively studied and several methods involving modification of the microorganism metabolism in order to increase terpene production have been developed.

In order to improve sesquiterpene production, several strategies were applied to augment the intracellular pool of the acyclic terpene precursor FPP available for terpene synthases. For example in yeast, as a large part of the FPP produced goes into the sterol producing pathway, several strategies have been developed to reduce the activity of the ERG9 gene, which codes for the squalene synthase (the first committed enzyme in sterol biogenesis).

Deletion of ERG9 has been envisaged. However, mutants in which ERG9 is deleted are unable to synthesize sterols. Such transformation therefore has the disadvantage that the obtained yeast strains are not viable unless they are fed with sterols.

In order to avoid deletion of the ERG9 gene, ERG9 mutants with a reduced activity have been used, for example in WO 2010/019696. However, even if the activity of ERG9 is sufficient to avoid sterols feeding, the reduced activity of ERG9 is detrimental to the yeast growth, the growth being considerably slowed down.

Another approach was to down-regulate ERG9 by replacing its native promoter by PMET3, a yeast L-methionine regulatable promoter. This strategy has been shown to enhance sesquiterpene production in yeast (Ro et al., Nature 2006, 440:940). However, this method has the disadvantage of requiring supplementing the growth medium with various concentrations of L-methionine depending on the desired level of ERG9 activity. The cost of L-methionine and its possible consumption by the cell constitute important drawbacks of such methods. In particular, the difficulties in controlling the METS promoter activity when the repressing agent L-methionine is metabolized by the cells are evidenced in comparative Example 6 of the present application.

It is an objective of the present invention to modulate expression of enzymes consuming terpene precursors in microorganisms, for example ERG9, in a way that enables optimal growth of the microorganism as well as maximal selective reduction of the desired gene activity during terpene production and that does not require supplementing the growth medium with additional feeding such as L-methionine or sterols.

SUMMARY OF THE INVENTION

In a first aspect, the invention provides a microorganism expressing at least one terpene synthase and comprising at least one endogenous gene encoding a protein that is not a terpene synthase, characterized in that the native promoter of the endogenous gene has been replaced by a heterologous glucose-regulated promoter;

said glucose-regulated promoter is induced by high glucose concentrations and repressed by low glucose concentrations; and said endogenous gene encodes a protein that uses an acylic terpene precursor as substrate.

In another aspect, the invention provides a glucose-limited fed batch fermentation process comprising cultivating a microorganism of the invention.

In a third aspect, the invention provides a method for producing a terpene compound comprising cultivating a microorganism of the invention in a glucose-limited fed batch fermentation process, the terpene synthase expressed by said microorganism being capable of catalysing the formation of said terpene compound.

In a fourth aspect, the present invention provides a method for increasing the production of a terpene compound in a microorganism comprising:

a) modifying said microorganism to replace the native promoter of an endogenous gene encoding a protein that is not a terpene synthase and that uses an acyclic terpene precursor as substrate by a glucose-regulated promoter, said glucose regulated promoter being induced by high glucose concentrations and repressed by low glucose concentrations, provided that said microorganism further expresses at least one terpene synthase capable of catalysing the formation of said terpene compound; and b) cultivating the transformed microorganism obtained in step a) in a glucose-limited fed-batch process.

DETAILED DESCRIPTION OF THE INVENTION

Figure 1:
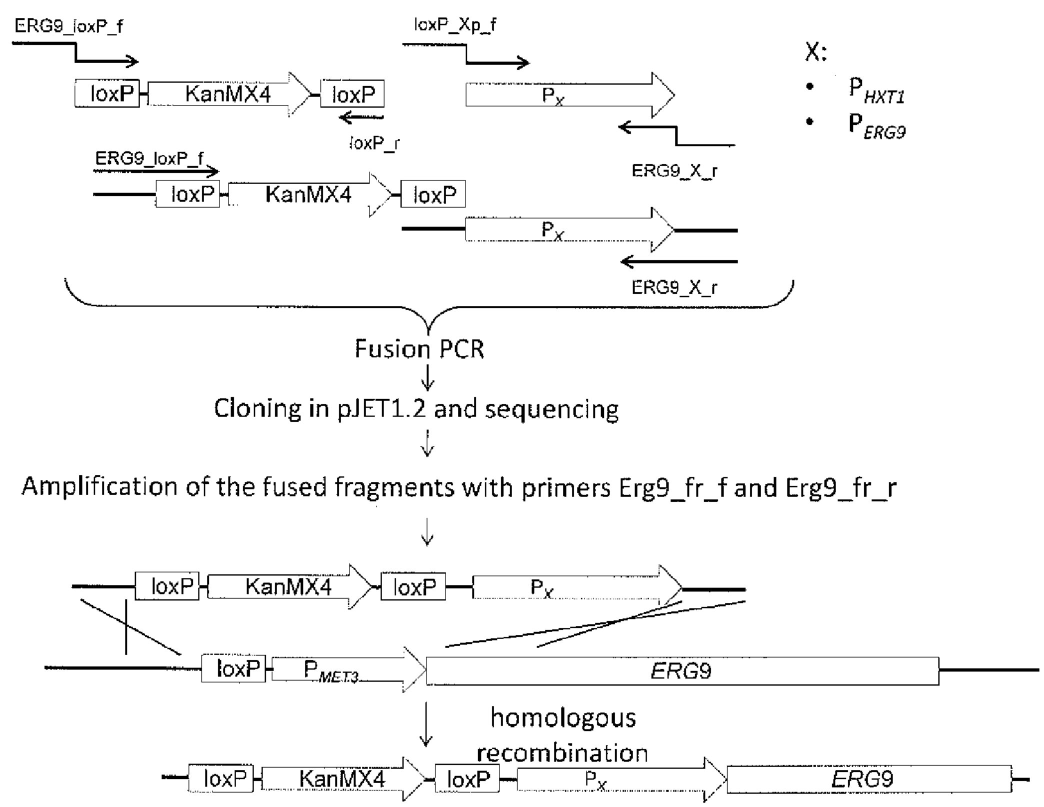
FIG. 1: Schematic drawing of the cloning strategy for the ERG9 promoter substitution.

The present invention provides a microorganism expressing at least one terpene synthase and comprising at least one endogenous gene encoding a protein that is not a terpene synthase wherein

- the native promoter of the endogenous gene has been replaced by a heterologous glucose-regulated promoter;
- the glucose-regulated promoter is induced by high glucose concentrations and repressed by low glucose concentrations; and
- the endogenous gene encodes a protein that uses an acyclic terpene precursor as substrate.

Any microorganism that can be cultivated in a glucose-containing medium, such as bacteria or yeast, is encompassed by the present invention. Preferably, the microorganism is yeast, more preferably it is selected from yeast of the *Saccharomyces, Zygosaccharomyces, Kluyveromyces, Candida, Hansenula, Debaryomyces, Mucor, Pichia* and *Torulopsis* genera. These yeast genera have the advantage of being industrially transformable and cultivable. Even more preferably it is yeast of the *Saccharomyces* genus and most preferably *Saccharomyces cerevisiae.*

For the purpose of the present invention, the microorganism must express at least one terpene synthase. As "terpene synthase" it is intended here any enzyme that is capable of catalysing the transformation of an acyclic terpene precursor into a terpene compound. The terpene compound can be produced as a single product or as part of a mixture of products. Preferably said terpene synthase is a monoterpene synthase (i.e. that is capable of catalysing the transformation of GPP to at least one monoterpene compound), a sesquiterpene synthase (i.e. that is capable of catalysing the transformation of FPP to a sesquiterpene compound) or a diterpene synthase (i.e. that is capable of catalysing the transformation of GGPP to a diterpene compound). Said terpene synthase must be functional, so that the microorganism is capable of catalysing the synthesis of a terpene compound from an acyclic terpene precursor using such terpene synthase. The terpene synthase can be either endogenous or exogenous and can be selected among all terpene synthases as defined above. In particular it can preferably be a monoterpene synthase, a sesquiterpene synthase or a diterpene synthase, more preferably it is a sesquiterpene synthase.

Examples of preferred sesquiterpene synthases include α-santalene synthase, patchoulol synthase, β-santalene synthase, valencene synthase, cubebol synthase, zizaene synthase, amorpha 4,11-diene synthase, humulene synthase, aristolochene synthase, bergamotene synthase, zingiberene synthase, farnesene synthase, caryophyllene synthase, isodaucene synthase, sesquithujene synthase, avermitilol synthase, eudesmol synthase, vetispiradiene synthase, longifolene synthase, cyclocopacamphene synthase, isolongifolene synthase, germacrene synthase, bicyclogermacrene synthase, bisabolol synthase, germacradienol synthase, hedycaryol synthase, barbatene synthase, epi-cedrol synthase, epi-aristolochene synthase, sesquisabinene synthase, cuprene synthase, selinene synthase, copaene synthase, macrocarpene synthase, cadinol synthase, intermedeol synthase, nerolidol synthase, muurola-3,5-diene synthase, curcumene synthase and epi-beta santalene synthase. More preferred sesquiterpene synthases include α-santalene synthase, patchoulol synthase, β-santalene synthase, valencene synthase, cubebol synthase, zizaene synthase, amorpha 4,11-diene synthase. Even more preferably, the sesquiterpene synthase is a patchoulol synthase or an α-santalene synthase. Most preferably, it is an α-santalene synthase.

Examples of preferred diterpene synthases include sclareol synthase, labdendiol synthase and taxadiene synthase. Examples of preferred monoterpene synthases include limonene synthase, pinene synthase, myrcene synthase, camphene synthase, phellandrene synthase, terpinolene synthase, ocimene synthase, linalool synthase, cineole synthase, geraniol synthase, terpinene synthase, fenchol synthase, carene synthase, sabinene synthase.

The endogenous gene of which the natural promoter is substituted is naturally present in the microorganism and encodes a protein that uses an acyclic terpene precursor as substrate. Such "acyclic terpene precursor" is intended as any precursor that is converted to terpene compounds under the action of a terpene synthase. Preferably it is geranyl pyrophosphate (GPP), farnesyl pyrophosphate (FPP) or geranyl geranyl pyrophosphate (GGPP). Most preferably, the acyclic terpene precursor is FPP.

As a "protein using an acyclic terpene precursor as substrate" it is intended for the purpose of the present invention any polypeptide that is capable of catalysing a reaction in which an acyclic terpene precursor is the starting material. A variety of genes having such an activity are found in microorganisms. The acyclic terpene precursor can be transformed chemically in different ways, depending on the protein that is involved in its transformation. Such proteins differ from one microorganism to the other. However, such proteins are well-known to the person skilled in the art. Examples of such proteins that can be found for example in yeast include prenyl transferases, farnesyltransferase, cis-prenyltransferase or squalene synthase.

Any gene that encodes a protein that uses such an acyclic terpene precursor as substrate can be modified for the purpose of the invention. However, said gene must not code for a terpene synthase. This ensures that modification of the gene expression enables to down-regulate the activity of said gene, while maintaining the highest possible activity of terpene synthases expressed by such microorganism.

In a preferred embodiment of the invention, the promoter-modified gene is a gene encoding a squalene synthase. For the purpose of the present invention a "squalene synthase" is defined as an enzyme capable of producing squalene from farnesyl pyrophosphate (FPP).

However, the promoter-modified gene can also be any other gene encoding for a protein that uses an acyclic terpene precursors as substrate. For example, when the microorganism is *S. cerevisiae*, the endogenous promoter-modified gene can be selected from genes encoding the prenyl transferases RAM1 or RAM2, the protein Coq1, the farnesyltransferase COX10, the cis-prenyltransferases SRT1 or RER2 or the squalene synthase ERG9. Most preferably it encodes ERG9. All of these specific enzymes are endogenous in *Saccharomyces cerevisiae* and use FPP as substrate.

The genetic modification of the gene consists in replacing its native promoter by a glucose-regulated promoter that is induced by high glucose concentrations and repressed by low glucose concentrations. For the purpose of the present invention, high glucose concentrations are defined as glucose concentrations of at least 1 gram of glucose per liter of culture medium and low glucose concentration as glucose concentrations below 1 gram of glucose per liter of culture medium. Preferably high glucose concentrations are defined as glucose concentrations of at least 10 grams of glucose per liter of culture medium and low glucose concentration as glucose concentrations below 1 gram of glucose per liter of culture medium.

The activity of the heterologous promoter is regulated by the concentration of the glucose present in the medium in which the microorganism is cultivated. These concentrations are particularly compatible with the use of the genes of the present invention in microorganisms cultivated in glucose-limited fed-batch fermentation processes, in which such high concentration of glucose are present in the growth medium during the batch phase, thus allowing for high activity of the regulated gene and rapid increase in biomass. Conversely, the promoter provides a reduced level of the regulated protein at low, growth-limiting glucose concentrations, allowing more acyclic terpene precursor, as defined in any of the above-described embodiments, to be utilized for the production of terpene compounds. Concentrations of glucose of less than 1 g per liter of culture medium are compatible with the low amounts of glucose present in the culture medium during the feeding phase of the fed-batch fermentation process because during that phase the glucose feeding is such that all the glucose fed to the medium is consumed by the microorganism, so that the concentration in the medium is close to 0 g/l.

The glucose-regulated promoter is heterologous. For the purpose of the present invention, a “heterologous promoter” means that in the modified organism such promoter regulates the expression of a gene that it does not regulate in the native microorganism. The promoter can originate from the same microorganism or from another microorganism. In the case where it originates from the same microorganism, it can be responsible for the regulation of the expression of any other gene of said microorganism. In a preferred embodiment, the glucose-regulated promoter originates from the same microorganism or from an organism having a similar philogeny. In a more preferred embodiment, the glucose-regulated promoter originates from the same microorganism.

Preferred promoters for use in the present invention are promoters that are found naturally in the microorganism in which the gene is present, but which regulate the activity of a different gene. More preferably, the promoter is found in yeast, even more preferably in a yeast of the *Saccharomyces* genus and most preferably in *Saccharomyces cerevisiae*. Most preferred promoters for use in the present invention are the hexose transporters 1 (HXT1), 3 (HXT3) and 4 (HXT4). Preferably, it is HXT1. Such promoters are extensively described in *J Biol Chem* 1999, 274:15350-15359.

The microorganism can optionally have undergone any other modification of its metabolism, and in particular of its terpene production metabolism. For example its native pathway leading to the formation of the acyclic terpene precursor can have been the object of genetic engineering in order to increase the amount of acyclic terpene precursor produced. As another example, a heterologous pathway leading to the production of such acyclic terpene precursor can have been introduced by genetic engineering into said microorganism. These genetic modifications may include but are not limited to: overexpression of a farnesyl diphosphate synthase (for example ERG20 in *S. cerevisiae*), overexpression of the catalytic domain of the rate-limiting enzyme 3-hydroxy-3-methylglutaryl-coenzyme A reductase (HMGR), overexpression of upc2-1, a semi-dominant mutant allele that enhances the activity of UPC2, a global transcription factor regulating sterol biosynthesis in *S. cerevisiae*, deletion of the genes encoding lipid phosphatases active on farnesyl diphosphate (suh as Lpp1 and Dpp1 in *S. cerevisiae*), deletion of the NADPH-dependent glutamate dehydrogenase encoded by GDH1 and simultaneous overexpression of the NADH-dependent glutamate dehydrogenase encoded by GDH2.

The microorganisms of the present invention are particularly advantageously cultivated using a glucose-limited fed-batch fermentation process. A glucose-limited fed-batch fermentation process comprising cultivating a microorganism of the invention, as defined in any of the above-described embodiments is therefore another object of the present invention.

Glucose-limited fed-batch fermentation processes are well-known to the person skilled in the art, so that it needs not be explained extensively in the present description. In any case, examples of conditions that can be applied for such type of fermentation are described in full details in the Examples of the present application. For the purpose of the present invention, a glucose-limited fed-batch fermentation process is intended as any fermentation process in which the microorganism is first grown in a batch phase in the presence of high, non-limiting concentrations of glucose, thus allowing rapid biomass formation, this phase being followed by a feeding phase in which the biomass is cultivated in the presence of low, growth-limiting glucose concentrations. Preferably, the concentration of glucose in the culture medium used in the batch phase is of at least 1 g/l, more preferably at least 10 g/l whereas the concentration of glucose in the culture medium used in the feeding phase is of less than 1 g/l.

The microorganism of the present invention, as defined in any of the above-described embodiments is also advantageously used in a method for producing a terpene compound comprising cultivating a microorganism of the invention in a glucose-limited fed batch fermentation process, as defined above. In such method the terpene synthase expressed by the microorganism is capable of catalysing the formation of the terpene compound that is intended to be produced. Such terpene synthase is as defined above in any embodiment of the invention. Most preferably, it is a sesquiterpene compound. Examples of sesquiterpene compounds include α-santalene, patchoulol, β-santalene, valencene, cubebol, zizaene, amorpha 4,11-diene, humulene, aristolochene, bergamotene, zingiberene, farnesene, caryophyllene, isodaucene, sesquithujene, avermitilol, eudesmol, vetispiradiene, longifolene, cyclocopacamphene, isolongifolene, germacrene, bicyclogermacrene, bisabolol, germacradienol, hedycaryol, barbatene, epi-cedrol, epi-aristolochene, sesquisabinene, cuprene, selinene, copaene, macrocarpene, cadinol, intermedeol, nerolidol, muurola-3,5-diene, curcumene and epi-beta santalene. More preferred sesquiterpene include α-santalene, patchoulol, β-santalene, valencene, cubebol, zizaene, amorpha 4,11-diene. Even more preferably, the sesquiterpene is patchoulol or α-santalene. Most preferably, it is α-santalene.

Examples of preferred diterpenes include sclareol, labdendiol and taxadiene. Examples of preferred monoterpenes include limonene, pinene, myrcene, camphene, phellandrene, terpinolene, ocimene, linalool, cineole, geraniol, terpinene, fenchol, careen and sabinene.

In a preferred embodiment of the invention, the method for producing a terpene compound comprises the following steps:

a) transforming a microorganism to replace the native promoter of an endogenous gene encoding a protein that uses an acyclic terpene precursor as substrate by a glucose-regulated promoter, said glucose regulated promoter being induced by high glucose concentrations and repressed by low glucose concentrations, provided that said gene does not encode a terpene synthase and provided that said microorganism further expresses at least one terpene synthase capable of catalysing the formation of said terpene compound;

b) cultivating the transformed microorganism obtained in step a) in a glucose-limited fed-batch fermentation process, so that the microorganism produces the terpene compound; and c) optionally isolating the terpene compound produced in step b)

In another embodiment, the invention provides for a method for increasing the production of a terpene compound in a microorganism comprising:

a) transforming said microorganism to replace the native promoter of an endogenous gene encoding a protein that uses an acyclic terpene precursor as substrate by a glucose-regulated promoter, said glucose regulated promoter being induced by high glucose concentrations and repressed by low glucose concentrations, provided that said gene does not encode a terpene synthase and provided that said microorganism further expresses at least one terpene synthase capable of catalysing the formation of said terpene compound; and b) cultivating the transformed microorganism obtained in step a) in a glucose-limited fed-batch fermentation process so that the microorganism produces the terpene compound.

In such method, the microorganism, the terpene compound, the gene, the promoter and the terpene synthase are all as defined in any of the above-described embodiment of the invention.

EXAMPLES

Example 1

ERG9 Promoter Replacement by the MET3 Promoter (Comparative Example)

The MET3 promoter was amplified from genomic DNA of *S. cerevisiae* CEN.PK 113-7D (MATa MAL2-8$^c$ SUC2 ura3-52) (BMC Genomics 2010 11:723) using the primers 1 and 2 (SEQ ID NO:1 and SEQ ID NO:2). The PCR conditions were in accordance with the Expand High Fidelity standard conditions (Roche Applied Science, Mannheim, Germany). Subsequently, the PCR fragments were digested by the restriction enzymes SpeI and SacII. In parallel, pUG6 plasmid (*Nucleic Acids Res* 1996, 24:2519-2524) was digested by the same couple of restriction enzymes. The DNA fragments were separated by gel electrophoresis and gel purified using the QIAEX1 II Gel extraction kit (Qiagen, Hilden, Germany). In vitro ligation of the digested plasmid with the digested PCR products was performed as the standard procedure given for T4 DNA ligase (Roche Applied Science). The resulting ligation mixture was used to transform chemically competent *E. coli* cells (DH5α) (Gene 1990, 96:23-28). Transformants were selected on LB medium supplemented with ampicillin (50 mg/L). The plasmid obtained was named pIP007.

The ERG9 gene is designated as YHR190W within the genome of CEN.PK 113-7D, as published in BMC Genomics 2010 11:723. The amino acid sequence of ERG9 encoded by this nucleic acid is published in GenBank, accession number: AAA34597.

In order to replace the native ERG9 promoter by the MET3 promoter, fusion PCR and a bipartite gene targeting method (*Genome Res* 1997, 7:1174-1183) were used. Four fragments were separately amplified before fusing them together in pairs. First, two fragments containing the MET3 promoter and the KanMX selection cassette were amplified from pIP007 in two separate, but overlapping fragments using the two couples of primers: primers 3 and 4 (SEQ ID NO:3 and 4) (Fragment A (SEQ ID NO:35)) and primers 5 and 6 (SEQ ID NO:5 and 6) (Fragment B (SEQ ID NO:36)). Furthermore, 500 by upstream of the ERG9 promoter in the genome of *S. cerevisiae* CEN.PK 113-7D (BMC Genomics 2010 11:723) were amplified using primers 7 and 8 (SEQ ID NO:7 and 8) (Fragment C (SEQ ID NO:37)). The first 500 by of the ERG9 ORF were as well amplified using primers 9 and 10 (SEQ ID NO:9 and 10) (Fragment D (SEQ ID NO:38)). The resulting four PCR fragments were gel-purified using the High Pure PCR Product Purification kit (Roche Applied Science) and subsequently fused together in pairs using fusion PCR. Fused fragments A and C (SEQ ID NO:39) were obtained after a fusion PCR using primers 4 and 7 (SEQ ID NO:4 and 7) while fused fragments B and D (SEQ ID NO:40) were obtained after a fusion PCR using primers 5 and 10 (SEQ ID NO:5 and 10). The two final fusion PCR fragments were gel purified with the High Pure PCR Product Purification kit.

*S. cerevisiae* strain CEN.PK113-5D (BMC Genomics 2010 11:723) was transformed with the obtained fusion PCR fragments to result in strain YIP-M0-04 (MATa MAL2-8$^c$ SUC2 ura3-52 $P_{ERG9}$Δ::kanMX-$P_{MET3}$). The loxP flanked kanMX cassette in strain YIP-M0-04 was then excised with the help of the Cre recombinase expression plasmid pSH47 as described by Güldener et al. (*Nucleic Acids Res.* 1996, 24:2519-2524).

To prevent the conversion of the isoprenoid precursor farnesyl pyrophosphate (FPP) into farnesol, the FPP phosphatase LPP1 (GenBank NM_001180811.1) was deleted in the YIP-M0-04 strain using a bipartite gene targeting strategy (*J Biol Chem.* 1999, 274:14831-14837; *Genome Res* 1997, 7:1174-1183). The 5' and 3' region of the LPP1 gene were amplified by PCR using primer pairs 11/12 (SEQ ID NO:11 and 12) (fragment 1 (SEQ ID NO:41)) and 13/14 (SEQ ID NO:13 and 14) (fragment 2 (SEQ ID NO:42)), respectively, and genomic DNA of CEN.PK113-5D as template (BMC Genomics. 2010 11:723). The 5' and the 3' part of the kanMX cassette were amplified from plasmid pUG6 using primer pairs 15/16 (SEQ ID NO:15 and 16) (fragment 3 (SEQ ID NO:43) and 17/18 (SEQ ID NO:17 and 18) (fragment 4 (SEQ ID NO:44)), respectively. Complementary primer tails allowed for the combination of fragments 1 and 3 (SEQ ID NO:45) by fusion PCR. Likewise, fragments 2 and 4 (SEQ ID NO:46) were fused to each other. Cells were transformed with both fusion PCR fragments and integration of the kanMX cassette at the LPP1 locus was tested by PCR using primers 19 and 20 (SEQ ID NO:19 and 20). Subsequent excision of the kanMX cassette led to formation of strain SCICK00 (MATa MAL2-8$^c$ SUC2 ura3-52 dpp1Δ::loxP $P_{ERG9}$Δ::loxP-$P_{MET3}$).

Example 2

Construction of a $P_{MET3}$ Reporter Strain

To construct an integrative plasmid carrying the reporter gene LacZ under the control of the MET3 promoter, the latter was amplified from genomic DNA of *S. cerevisiae* CEN.PK 113-7D using the primers 1' and 2' (SEQ ID NO:33 and 34), restricted with HindIII/NotI and ligated into HindIII/NotI cut pSF011 plasmid resulting in pSF011-$P_{MET3}$ (Yeast 2010, 27: 955-964). A yeast strain carrying a genomic integration of LacZ under the control of the MET3 promoter was constructed by transforming CEN.PK 113-7D with the NcoI restricted integrative plasmid pSF011-$P_{MET3}$ resulting in strain SCICK10 (MATa MAL2-8$^c$ SUC2 ura3-52::pSF011-$P_{MET3}$).

Example 3

ERG9 Promoter Substitution by the HXT1 Promoter

The strain described above was used for further promoter substitutions using the strategy depicted in FIG. 1.

To replace the ERG9 controlling MET3 promoter in SCICK00, the ERG9 promoter and the HXT1 promoter were amplified from CEN.PK113-5D genomic DNA by PCR using primer pairs 21/22 (SEQ ID NO:21 and 22) and 23/24 (SEQ ID NO:23 and 24), respectively. In addition the kanMX cassette was amplified in a PCR reaction containing primers 25 and 26 (SEQ ID NO:25 and 26). The marker cassette was combined with either of the two promoters by fusion PCR and the resulting fragments were amplified once more using primers 27 and 28 (SEQ ID NO:27 and 28) in order to extend the flanking regions for genomic integration (ERG9 fusion (SEQ ID NO:47) and HXT1 fusion fragments (SEQ ID NO:48). After successful fusion, the fragments were cloned into pJET1.2 (Fermentas GMBH) and sequenced. Transformation of SCICK00 with these fusion PCR fragments and subsequent excision of the kanMX cassette resulted in strains SCICK01 (MATa MAL2-8$^c$ SUC2 ura3-52 dpp1Δ::loxP $P_{ERG9}$Δ::loxP-$P_{HXT1}$) and SCICK03 (MATa MAL2-8$^c$ SUC2 ura3-52 dpp1Δ::loxP $P_{ERG9}$Δ::loxP-$P_{ERG9}$).

Example 4

Construction of an (+)-α-Santalene and tHMG1 Yeast Expression Vector

To construct the (+)-α-santalene expression vector, the santalene synthase cDNA was amplified by PCR from plasmid Cont2B-27-pET101 (WO 2009109597, GenBank accession number: HQ452480), using primers 29 and 30 (SEQ ID NO:29 and 30), cut with NotI/PacI and ligated into NotI/PacI restricted vector pSP-G1 (Yeast 2010, 27:954-965). Subsequently, tHMG1 was PCR amplified using genomic DNA of *S. cerevisiae* CEN.PK113-5D as template and primers 31 and 32 (SEQ ID NO:31 and 32), cut with BamHI/NheI and ligated into the same vector after restriction with BamHI and NheI (*Nature* 2006, 440:940-943). This resulted in formation of the expression plasmid pICK01. pICK01 was then transformed in SCICK00, SCICK01 and SCICK03 resulting in strains SCICK12 (MATa MAL2-8$^c$ SUC2 ura3-52 dpp1Δ::loxP $P_{ERG9}$Δ::loxP-$P_{HXT1}$), SCICK13 (MATa MAL2-8$^c$ SUC2 ura3-52 dpp1Δ::loxP $P_{ERG9}$Δ::loxP-$P_{ERG9}$) and SCICK15 (MATa MAL2-8$^c$ SUC2 ura3-52 dpp1Δ::loxP $P_{ERG9}$Δ::loxP-$P_{MET3}$), respectively.

Example 5

Glucose-Limited Fed Batch Cultivation

For batch cultivations, a previously described (*Yeast* 1992, 8:501-517) mineral salts medium was used consisting of the following: $(NH_4)_2SO_4$ (5 g/l); $KH_2PO_4$ (3 g/l); $MgSO_4.7H_2O$ (0.50 g/l); Antifoam 289 (Sigma-Aldrich) (0.050 ml/l); trace metals (1 ml/l) and vitamins 1.0 ml/l. The trace metal solution consisted of the following: EDTA (sodium salt) (15.0 g/l); $ZnSO_4.7H_2O$ (0.45 g/l); $MnCl_2.2H_2O$ (1 g/l); $CoCl_2.6H_2O$ (0.3 g/l); $CuSO_4.5H_2O$ (0.3 g/l); $Na_2MoO_4.2H_2O$ (0.4 g/l); $CaCl_2.2H_2O$ (0.45 g/l); $FeSO_4.7H_2O$ (0.3 g/l); $H_3BO_3$ (0.1 g/l) and KI (0.10 g/l). The pH of the trace metal solution was adjusted to 4.0 with 2M NaOH prior to heat sterilization. The vitamin solution consisted of the following: biotin (0.05 g/l); p-amino benzoic acid (0.2 g/l); nicotinic acid (1 g/l); Ca-pantothenate (1 g/l); pyridoxine-HCl (1 g/l); thiamine-HCl (1 g/l) and myo-inositol (25 g/l). The pH of the vitamin solution was adjusted to 6.5 with 2M NaOH. The vitamin solution was filter sterilized and stored at 4° C. This medium was supplemented with 30 g/l glucose. The feed composition used for fed-batch cultivation had the same composition as described above, but the $(NH_4)_2SO_4$; $KH_2PO_4$; $MgSO_4.7H_2O$, vitamin solution, and trace metal solution, concentration were increased 10 times. The glucose concentration was 200 g/l.

The seed cultures for the cultivations were grown at 30° C. in 500 ml shake flasks containing 100 ml of culture with agitation in an orbital shaker at 100 rpm. Per-cultures were used to inoculate the fermentors to a final dry weight of 1 mg/l.

The aerobic fed-batch process was performed in 2.5 liter Applikon vessels (Applikon, Schiedam, the Netherlands) with a working volume of 1.0 liter. Agitation at 600 rpm was maintained using an integrated magnetic stirrer (DasGip, Julich, Germany) and the temperature kept at 30° C. The rate of aeration was set to 0.61/min. The pH of the medium was maintained at 5.0 by automatic addition of 2 N KOH during the batch phase and 10% $NH_4OH$ during the feed phase. The temperature, agitation, gassing, pH and composition of the off-gas were monitored and controlled using the DasGip monitoring and control system. Dissolved oxygen concentration was monitored with a polarographic oxygen electrode (Mettler Toledo, Columbus, Ohio, USA) and kept above 30% via stirrer speed and gas flow rate using the DasGip control system. The effluent gas from the fermentation was analyzed for real-time determination of oxygen and $CO_2$ concentrations by DasGip fedbatch Pro® gas analysis systems with the off gas analyzer GA4 based on zirconium dioxide and two-beam infrared sensor.

The fed-batch cultures were initiated as batch culture using 30 g/l glucose, feeding with fresh medium commenced only after residual ethanol produced from the glucose consumption phase was completely depleted. A feed strategy was designed keeping the volumetric growth rate constant. An exponential feed rate v(t) (1/h) was calculated according to the following equation:

$$v(t) = \frac{Y_{xs}\mu_0}{s_f - s_0} x_0 V_0 \exp(\mu_0 t)$$

where $x_0$, $s_0$ and $V_0$ were the biomass density (g DCW/l), the substrate concentration (g/l) and the reactor volume (1) at the start of the fed-batch process, Yxs was the respiratory yield coefficient (g glucose/g DCW); $s_f$ was the concentration of the growth limiting substrate (g glucose/l) in the reservoir; $\mu_0$ was the specific growth rate ($h^{-1}$) during the feed phase and t the feeding time expressed in hours. According to the equation above, the feed was increased exponentially with a specific feed rate of 0.06 $h^{-1}$. Correct feed rate addition was obtained programming the fermentor fb-pro software (DasGip) and controlled using the DasGip control system. Under the feeding conditions, the glucose concentrations in the fermentor are maintained under 1 g/L allowing a repression of ERG9 expression. An organic layer of dodecane (Sigma-Aldrich St. Louis, Mo.) was added aseptically to a final volume of 10% (v/v) immediately before starting the feed.

Example 6

Functional Characterization of the MET3 Promoter (Comparative Example)

Figure 2:
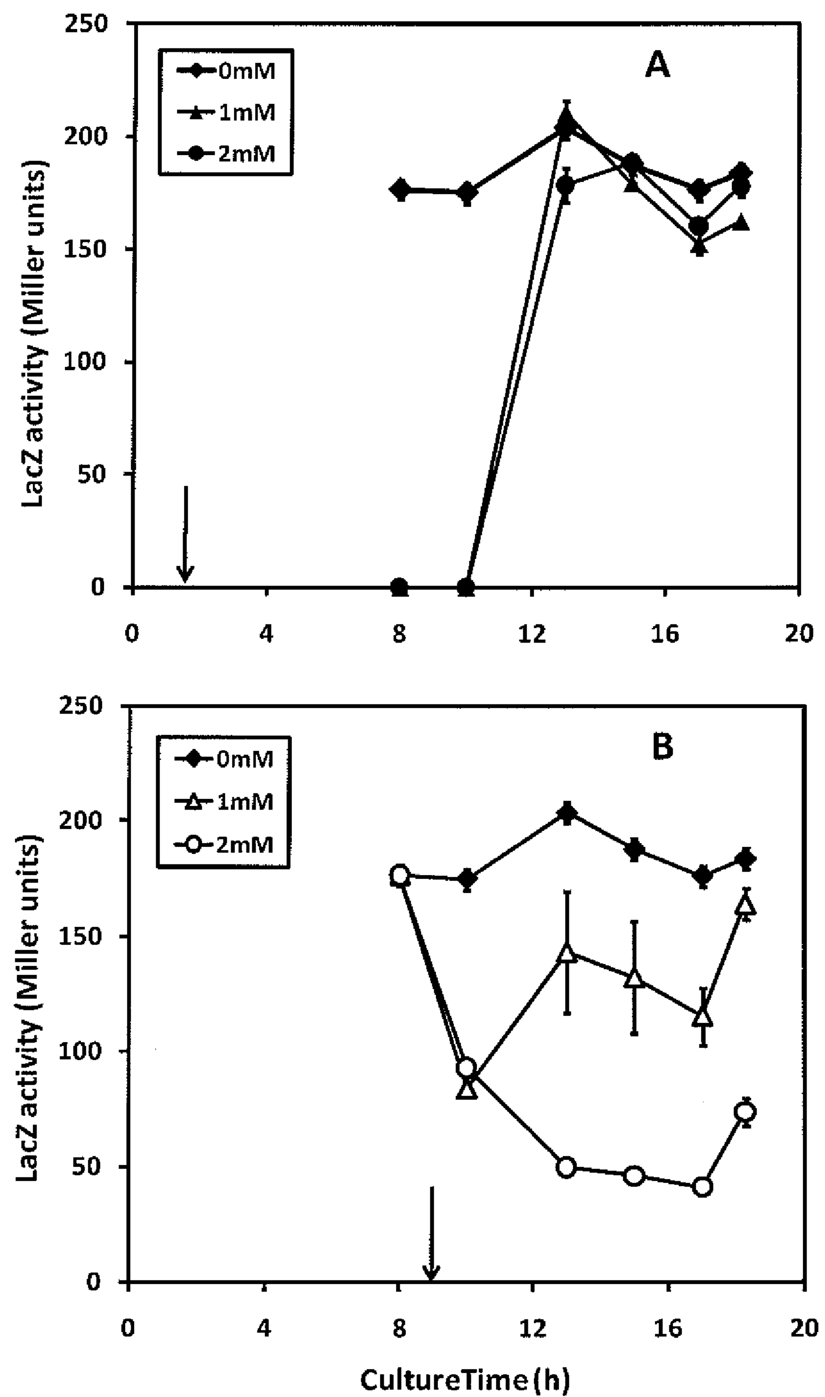
FIG. 2: LacZ activity in strain SCICK10 ($P_{MET3}$-lacZ) in response to different methionine concentrations, 0 mM (diamond), 1 mM (triangle) and 2 mM (circle), added respectively at 0 hours (A) and 8 hours (B) of cultivation. Arrows represent the time point of methionine addition.

The level of repression of the MET3 promoter throughout batch cultivation was determined by fusing $P_{MET3}$ to the LacZ reporter gene followed by measuring the β-galactosidase activity as described earlier (*Yeast* 2009, 26:545-551). In previous studies, $P_{MET3}$-LacZ exhibited different levels of expression depending on the concentration of methionine supplied (*Curr Microbiol* 2002, 45:37-40). In order to evaluate the correct supply of methionine required to reduce the LacZ expression, strain SCICK10 was cultivated in shake flasks without L-methionine, with 1 mM and 2 mM L-methionine as initial concentration, and with 1 mM and 2 mM L-methionine added when the cultures had reached an $OD_{600}$ of 0.6. The concentrations of the inhibitor were chosen based on the amounts previously used for ERG9 repression (*Biotechnol Bioeng* 2007, 993:666-677). As shown in FIG. 2A, the β-galactosidase activity was constant in the cultures not containing L-methionine. In the cultures that contained L-methionine from the beginning, LacZ activity was initially very low. However, at about mid-exponential phase, it started to increase and rapidly reached the levels measured in the non-repressed culture. When L-methionine was added at a later stage, LacZ activity dropped to a lower level in the culture pulsed with 2 mM L-methionine than in the culture pulsed with 1 mM L-methionine, but in both cases it started to increase again towards the end of the cultivation (FIG. 2B).

These results demonstrate the difficulties in controlling the MET3 promoter activity when the repressing agent is metabolized by the cells. We therefore tested, if D-methionine or 2-hydroxy-4-(methylthio)butyric acid could serve as L-methionine analogues to repress the $P_{MET3}$ promoter, because they may not be metabolized by yeast or metabolized to a lesser extent. At concentrations of up to 4 mM in the medium neither of the two compounds had the capability to reduce $P_{MET3}$ activity (data not shown). These results confirm the interest of finding an alternative solution to the regulation of gene activity using the MET3 promoter.

Example 7

Evaluation of the HXT1 Promoter to Control ERG9 Expression in Fed Batch Fermentation Three strains were constructed. Strain SCICK13 in which ERG9 is under the control of its native promoter served as a reference strain. In strains SCICK15 and SCICK12, the ERG9 promoter had been replaced by the MET3 and HXT1 promoter, respectively. In order to maintain ERG9 repressed in the SCICK15 culture during the fermentation, L-methionine was added at regular interval every 6 hours to a final concentration of 2 mM.

All strains carried a deletion in the phosphatase encoding LPP1 gene to reduce the loss of FPP to farnesol (*J Biol Chem* 1999, 274:14831-14837). tHMG1 and (+)-α-santalene synthase were expressed from a high copy plasmid under control of the PGK1 and TEF1 promoters, respectively.

The physiological characterization of the strains was completed in aerobic glucose limited fed batch culture. A fed batch in situ product removal (ISPR) reactor mode consisting in an aqueous/dodecane two phase partitioning system was chosen to evaluate the (+)-α-santalene production capacity of these strains engineered to accumulate FPP. (+)-α-santalene production during the course of fermentation was determined as described previously in *Biotechnol Bioeng* 2010, 106:86-96. Samples from the organic layer were centrifuged 5 minutes at 5000 g and the supernatants were analyzed by gas chromatography-mass spectrometry (GC/MS) with a DSQ II single quadrupole mass spectrometer (Thermo Scientific, Waltham, Mass.). Analytes from 1 μl sample were separated on a SLB-5 ms capillary column (15 m, 0.25 mm i.d., 0.25 μm film thickness; Supelco, Bellefonte, Pa., USA) using helium as carrier gas at a flow rate of 1.2 ml $min^{-1}$. A split/splitless injector was used in the splitless mode. The initial oven temperature was 80° C. and the injector temperature was 250° C. The oven temperature was increased to 120° C. at a rate of 10° C./min and subsequently increased to 160° C. at a rate of 3° C./min. The oven temperature was finally increased to 270° C. at a rate of 10° C./min and held for 5 minutes at this temperature. Full mass spectra were generated by scanning m/z range within 40-500 for metabolite identification. Quantification of (+)-α-santalene and E,E-farnesol was carried out using standard curves.

For the extraction of sterols, a previously described method (*Biotechnol Bioeng* 2010, 106:86-96) was used with minor modifications. Known volumes of fermentation broth were harvested by centrifuging at 5,000 rpm for 10 minutes. The cell pellet was washed twice with distilled water and the cell suspension was centrifuged for another 10 minutes at 5,000 rpm. The cell pellet was resuspended in 4 ml of 0.2 N HCl and heated in a water bath at 85° C. for 1 h and then allowed to cool to room temperature. After centrifugation for 10 minutes at 5,000 rpm and removal of the supernatant, the cell pellet was resuspended in 2 nil methanol containing 0.2% (w/v) pyrogallol and 1 ml 4 N KOH and transferred to a 14 ml glass vial sealed with a PTFE lined screw cap, heated again for 2 hours in a water bath at 85° C. for saponification and then cooled to room temperature. Sterols were extracted by addition of 5 ml heptane followed by vigorous mixing for 2 minutes. After 2 hours, the n-heptane layer was transferred to a new glass vial for HPLC analyses. Quantitative determination of total ergosterol was carried out by isocratic high-performance liquid chromatography (UltiMate® 3000 Nano, Dionex) with a reverse phase Develosil column (C30-UG-5; Nomura Chemicals, Aichi, Japan) at 40° C. using 70% MeOH as the mobile phase at a flow rate of 1 nil $min^{-1}$. Ergosterol concentration was measured with a UV-visible light absorbance detector set at 280 nm (Photodiode Array Detector, Dionex). The amount of ergosterol was determined with Dionex Chromeleon® software using absolute calibration curves.

Figure 3:
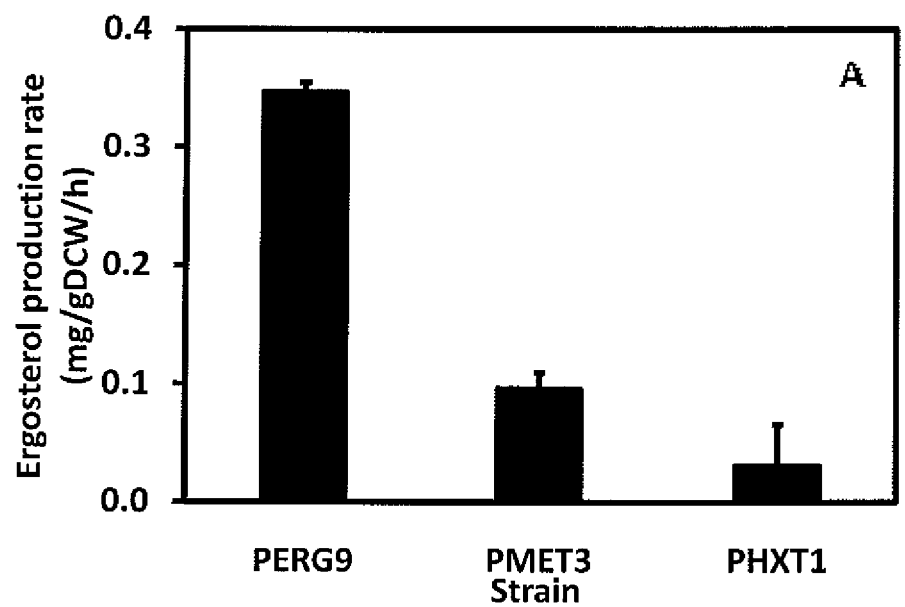
FIG. 3: Ergosterol production rate (g·g biomass$^{-1}$·h$^{-1}$) (A) and α-(+)-santalene and E,E-farnesol production rate (g·g biomass$^{-1}$·h$^{-1}$) (B) in strains SCICK13 ($P_{ERG9}$), SCICK15 ($P_{MET3}$) and SCICK12($P_{HXT1}$).
Figure 3:
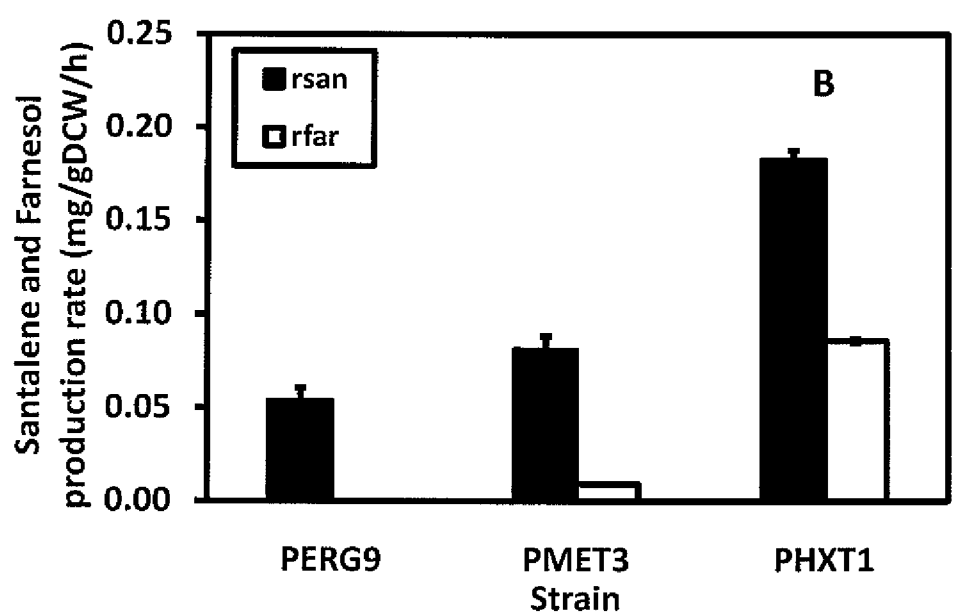

The effect of the above mentioned strategies for down-regulation of ERG9 was evaluated by comparing the obtained yield of (+)-α-santalene during the feed phase. Samples were taken from the dodecane phase, analysed by GC-MS and quantified using a standard curve with different dilutions of a (+)-α-santalene standard. All transformed strains were able to synthesize (+)-α-santalene. Two major chromatographic peaks were detected in all the strains transformed with the expression vector corresponding in retention time and mass spectra to those of (+)-α-santalene and E,E-farnesol. Cultivation was started as batch with 30 g/l glucose. After complete glucose consumption and after residual ethanol produced during the glucose consumption phase was completely depleted, the organic layer was added to the fermentor and the production phase was started by initiating a feed of fresh concentrated substrate with exponential kinetics for a total feed period of 36 hours. Within the first 30 hours of feed the culture metabolism was completely respiratory characterized by complete oxidation of glucose with biomass and carbon dioxide as the major products and complete absence of fermentation products, while the respiratory coefficients remained close to 1 for all strains. After that a limitation phase occurred where yeast growth was no longer consistent with the feeding profile determining a shift towards a fermentative metabolism resulting in accumulation of glucose and ethanol production. To examine the effect of ERG9 repression on the sterol pathway the total cellular sterol content was measured. Engineered strains exhibited significant changes in the level of ergosterol production. A lower sterol content was observed in the two $P_{ERG9}$ replacement mutants compared to the strain bearing the original ERG9 promoter. The lowest sterol content was observed in strain SCICK12 ($P_{HXT1}$) (microorganism according to the invention) with a 11-fold reduction while the MET3 promoter (strain SCICK15) led to a modest 3-fold decrease (FIG. 3A).

To establish if the lower sterol content reflected an increased availability of FPP precursor for sesquiterpene conversion, product accumulation in the organic layer was measured. A linear correlation was observed between the reduction in ergosterol content and the increase in (+)-α-santalene production. Different levels of ERG9 repression diverted FPP towards (+)-α-santalene formation, redirecting the flux distribution from the sterol pathway to sesquiterpene production. Strain SCICK12 ($P_{HXT1}$) was the best (+)-α-santalene producer with a 3.4-fold and 2.3-fold improvement in (+)-α-santalene productivity compared to SCICK13 ($P_{ERG9}$) and SCICK15 ($P_{MET3}$), respectively (FIG. 3B). These results show that the advantages of the present invention are two-fold when compared to the use of the MET3 promoter, which is already known from the prior art. Indeed, firstly the cultivation method is simplified because it is not necessary to feed the culture medium with methionine and secondly the production rate of the terpene compound is increased.

What is claimed is:

1. A method for producing a terpene compound comprising cultivating a *Saccharomyces cerevisiae* yeast expressing at least one terpene synthase and comprising at least one endogenous gene encoding squalene synthase ERG9, wherein i) the native promoter of the endogenous gene has been replaced by a hexose transporter 1 (HTX1) promoter;

ii) the HTX1 promoter is induced by high glucose concentrations and repressed by low glucose concentrations; and iii) the endogenous gene encodes a protein that uses an acrylic terpene precursor selected from the group consisting of geranyl pyrophosphate (GPP), farnesyl pyrophosphate (FPP) or geranyl geranyl pyrophosphate (GGPP) as a substrate;

in a glucose-limited fed batch fermentation process, the terpene synthase expressed by said yeast being capable of catalysing the formation of said terpene compound, wherein said terpene compound is selected from the group consisting of α-santalene, patchoulol, β-santalene, valencene, cubebol, zizaene, amorpha 4,11-diene, humulene, aristolochene, bergamotene, zingiberene, farnesene, caryophyllene, isodaucene, sesquithujene, avermitilol, eudesmol, vetispiradiene, longifolene, cyclocopacamphene, isolongifolene, germacrene, bicyclogermacrene, bisabolol, germacradienol, hedycaryol, barbatene, epi-cedrol, epi-aristolochene, sesquisabinene, cuprene, selinene, copaene, macrocarpene, cadinol, intermedeol, nerolidol, muurola-3,5-diene, curcumene and epi-beta santalene.

2. The method of claim 1, wherein the acyclic terpene precursor is FPP.

3. The method of claim 1, wherein the HTX1 promoter is induced by glucose concentrations of at least 1 gram per liter of culture medium and repressed by glucose concentrations of less than 1 gram per liter of culture medium.

4. A method for increasing the production of a terpene compound in a *Saccharomyces cerevisiae* yeast comprising a) transforming the yeast to replace a native promoter of an endogenous gene encoding a protein that uses an acyclic terpene precursor selected from the group consisting of geranyl pyrophosphate (GPP), farnesyl pyrophosphate (FPP) or geranyl geranyl pyrophosphate (GGPP) as a substrate by hexose transporter 1 (HTX1) promoter, said HTX1 promoter being induced by high glucose concentrations and repressed by low glucose concentrations, provided that said endogenous gene does not encode a terpene synthase, but encodes a protein selected from the group consisting of the prenyl transferases RAM1 and RAM2, the hexaprenyl diphosphate synthase Coq1, the famesyltransferase COX10, the cisprenyltranferases SRT1 and RER2, and the squalene synthase ERG9, and provided that said yeast further expresses at least one terpene synthase capable of catalysing the formation of said terpene compound, wherein said terpene compound is selected from the group consisting of α-santalene, patchoulol, β-santalene, valencene, cubebol, zizaene, amorpha 4,11-diene, humulene, aristolochene, bergamotene, zingiberene, farnesene, caryophyllene, isodaucene, sesquithujene, avermitilol, eudesmol, vetispiradiene, longifolene, cyclocopacamphene, isolongifolene, germacrene, bicyclogermacrene, bisabolol, germacradienol, hedycaryol, barbatene, epi-cedrol, epi-aristolochene, sesquisabinene, cuprene, selinene, copaene, macrocarpene, cadinol, intermedeol, nerolidol, muurola-3,5-diene, curcumene and epi-beta santalene; and b) cultivating the transformed yeast obtained in step a) in a glucose-limited fed-batch fermentation process, so that the yeast produces the terpene compound; and c) optionally isolating the terpene compound produced in step b).

5. The method of claim 4, wherein the terpene compound is a sesquiterpene compound and wherein the terpene synthase is a sesquiterpene synthase.

6. The method of claim 1, wherein the terpene compound is a sesquiterpene compound and wherein the terpene synthase is a sesquiterpene synthase.

7. The method of claim 1, wherein the terpene compound is selected from the group consisting of α-santalene, patchoulol, β-santalene, valencene, cubebol, zizaene, and amorpha 4,11-diene.

8. The method of claim 4, wherein the terpene compound is selected from the group consisting of α-santalene, patchoulol, β-santalene, valencene, cubebol, zizaene, and amorpha 4,11-diene.

9. The method of claim 4, wherein the acyclic terpene precursor is FPP.

10. The method of claim 4, wherein the endogenous gene comprises a sequence encoding squalene synthase ERG9.

11. The method of claim 1, further comprising isolating the terpene compound produced by the yeast in the fermentation process.

12. The method of claim 1, wherein the terpene compound is α-santalene or β-santalene.

13. The method of claim 4, wherein the terpene compound is α-santalene or β-santalene.

* * * * *